(12) United States Patent
Agarwal et al.

(10) Patent No.: US 10,648,035 B2
(45) Date of Patent: May 12, 2020

(54) METHODS AND COMPOSITIONS FOR DIAGNOSING AND TREATING GASTRIC CANCER

(71) Applicant: THE JOHNS HOPKINS UNIVERSITY, Baltimore, MD (US)

(72) Inventors: Rachana Agarwal, Ellicott City, MD (US); Stephen J. Meltzer, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 809 days.

(21) Appl. No.: 14/646,774

(22) PCT Filed: Nov. 26, 2013

(86) PCT No.: PCT/US2013/071935
§ 371 (c)(1),
(2) Date: May 22, 2015

(87) PCT Pub. No.: WO2014/082067
PCT Pub. Date: May 30, 2014

(65) Prior Publication Data
US 2015/0292029 A1    Oct. 15, 2015

Related U.S. Application Data

(60) Provisional application No. 61/729,772, filed on Nov. 26, 2012.

(51) Int. Cl.
*C12Q 1/68* (2018.01)
*C12Q 1/6886* (2018.01)
*G01N 33/574* (2006.01)

(52) U.S. Cl.
CPC ..... *C12Q 1/6886* (2013.01); *G01N 33/57446* (2013.01); *C12Q 2600/154* (2013.01); *C12Q 2600/16* (2013.01); *G01N 2440/12* (2013.01)

(58) Field of Classification Search
None
See application file for complete search history.

(56) References Cited

U.S. PATENT DOCUMENTS

| | | | |
|---|---|---|---|
| 7,939,263 | B2 | 5/2011 | Clarke et al. |
| 2006/0246466 | A1 | 11/2006 | Sandvik et al. |
| 2007/0259368 | A1 | 11/2007 | An et al. |
| 2008/0081333 | A1 | 4/2008 | Mori et al. |
| 2009/0061441 | A1 | 3/2009 | Hoon et al. |
| 2009/0304697 | A1 | 12/2009 | Paik et al. |
| 2010/0009858 | A1 | 1/2010 | Li |
| 2010/0075334 | A1 | 3/2010 | Kim et al. |
| 2010/0196895 | A1 | 8/2010 | Kinoshita et al. |
| 2011/0151443 | A1 | 6/2011 | Sung et al. |
| 2011/0207122 | A1 | 8/2011 | Kinoshita et al. |
| 2012/0196827 | A1 | 8/2012 | Van Criekinge et al. |
| 2013/0022974 | A1* | 1/2013 | Chinnaiyan ......... C12Q 1/6886 435/6.11 |

FOREIGN PATENT DOCUMENTS

| | | | |
|---|---|---|---|
| WO | 2005001126 A1 | | 1/2005 |
| WO | WO2005/042713 | * | 5/2005 |
| WO | 2008100913 A2 | | 8/2008 |
| WO | 2008157437 A1 | | 12/2008 |
| WO | 2009034481 A2 | | 3/2009 |
| WO | 2009091023 A1 | | 7/2009 |

OTHER PUBLICATIONS

Rauch et al; PNAS, vol. 105, pp. 252-257, 2008.*
Agarawal (Molecular and Cellular Biology, abstract LB-384; Mar. 31, 2012).*
Resende, C., et al., "Genetic and Epigenetic Alteration in Gastric Carcinogenesis", Helicobacter (2010) vol. 15, Supplement 1, pp. 34-39.
Kober, P., et al., "Methyl-CpG Binding Column-Based Identification of Nine Genes Hypermethylated in Colorectal Cancer", Molecular Carcinogenesis (2011) vol. 50, No. 11, pp. 846-856.
Kang, G., et al., "DNA methylation profiles of gastric carcinoma characterized by quantitative DNA methylation analysis", Laboratory Investigation (2008) vol. 88, No. 2, pp. 161-170.
Gould, D., et al., "Cloning, characterization, localization, and mutational screening of the human BARX1 gene", Genomics, vol. 68, pp. 336-342, (2000).
Kim, B., et al., "The stomach mesenchymal transcription factor Barx1 specifies gastric epithelial identity through inhibition of transient Wnt signaling", Developmental Cell, (2005) vol. 8, No. 4, pp. 611-622.
Hartmann, O., et al., "DNA methylation markers predict outcome in node-positive, estrogen receptor-positive breast cancer with adjuvant anthracycline-based chemotherapy", Clinical Cancer Research: an official journal of the American Association for Cancer Research, (2009) vol. 15, No. 1, pp. 315-323.
Furuta, J., et al., "Silencing of Peroxiredoxin 2 and aberrant methylation of 33 CpG islands in putative promoter regions in human malignant melanomas", Cancer Research, Jun. 15, 2006, vol. 66, No. 12, pp. 6080-6086.

(Continued)

Primary Examiner — Jehanne S Sitton
(74) Attorney, Agent, or Firm — Johns Hopkins Technology Ventures

(57) ABSTRACT

The present invention relates to the field of gastric cancer. More specifically, the present invention provides methods and compositions for diagnosing and treating gastric cancer. In a specific embodiment, a method for diagnosing gastric cancer or a likelihood thereof in a patient comprises the steps of (a) providing a sample from the patient; (b) measuring the methylation levels of one or more biomarkers in the sample collected from the patient; and (c) predicting gastric cancer in the patient if the biomarkers are hypermethylated. In a more specific embodiment, the one or more biomarkers comprises tight junction protein claudin-11 (CLD-N11), the transcription factor BarH-like homeobox (BARX1), basonuclin1 (BNC1), Coagulation factor C homolog (COCH), filamin C gamma (FLNC), cytoglobin B (CYGB), glutamine-fructose-6-phospahe-transaminase-2 (GFPT2), heat-shock-70 kDa protein-6 (HSPA6), snail homolog 1 (SNAL1), skin calmodulin-related factor (SCARF), and tumor protein p53 binding protein 2 (TP53BP2).

14 Claims, 23 Drawing Sheets

(56) References Cited

OTHER PUBLICATIONS

Akino, K., et al., "Identification of DFNA5 as a target of epigenetic inactivation in gastric cancer", Cancer Science, Jan. 2007, vol. 98, No. 1, pp. 88-95.
Estecio, M., et al., "High-throughput methylation profiling by MCA coupled to CpG island microarray", Genome Research, (2007) vol. 17, pp. 1529-1536.
Mori, Y., et al., "Novel candidate colorectal cancer biomarkers identified by methylation microarray-based scanning", Endocrine Related Cancer, Aug. 2011, vol. 18, No. 4, pp. 465-478.
Toyota, M. et al., "Aberrant methylation in gastric cancer associated with the CpG island methylator phenotype", Cancer Research, Nov. 1, 1999, vol. 59, pp. 5438-5442.
Li, Q. et al., "Causal relationship between the loss of RUNX3 expression and gastric cancer" Cell, Apr. 5, 2002, vol. 109, pp. 113-124.
Tamura, G., "Genetic and epigenetic alterations of tumor suppressor and tumor-related genes in gastric cancer", Histology and Histopathology, (2002) vol. 17, pp. 323-329.
Kim, T., "Transcriptional silencing of the DLC-1 tumor suppressor gene by epigenetic mechanism in gastric cancer cells", Oncogene, (2002) vol. 22, pp. 3943-3951.
Yasui, W., et al., "Molecular-pathological prognostic factors of gastric cancer: a review", Gastric Cancer, (2005), vol. 8, pp. 86-94.
Nojima, M., et al., "Frequent epigenetic inactivation of SFRP genes and constitutive activation of Wnt signaling in gastric cancer", Oncogene (2007), vol. 26, pp. 4699-4713.

* cited by examiner

| GENE SYMBOL-NAME | SNU vs HFE145 | SNU-1 vs HFE145 | AGS vs HFE145 | MKN28 vs HFE145 | KATOIII vs HFE145 | HFE145 vs SNU | HFE145 vs SNU-1 | HFE145 vs AGS | HFE145 vs MKN28 | HFE145 vs KATOIII |
|---|---|---|---|---|---|---|---|---|---|---|
| BARX1-BarH-LIKE HOMEOBOX 1 | 14.72 | 5.46 | 4.35 | 7.57 | 14.12 | 3.12 | 3.05 | 3.64 | 3.16 | 3.08 |
| BNC1-BASONUCLIN 1 | 6.36 | 4.38 | 4.29 | 5.86 | 6.32 | 2.60 | 3.00 | 3.03 | 2.86 | 2.93 |
| CLDN11-CLAUDIN 11 | 8.57 | 4.82 | 5.7 | 9.32 | 14.52 | 16.62 | 16.73 | 16.06 | 17.24 | 16.67 |
| COCH-COAGULATION FACTOR C HOMOLOG | 5.74 | 3.14 | 4.5 | 2.5 | 2.48 | 3.05 | 3.41 | 3.59 | 3.23 | 3.35 |
| CYGB-CYTOGLOBIN | 14.83 | 5.5 | 6.45 | 11.71 | 10.56 | 1.83 | 2.08 | 3.28 | 2.50 | 2.55 |
| FLNC-FILAMIN C, GAMMA | 6.19 | 2.08 | 2.66 | 3.66 | 11.79 | 106.89 | 133.10 | 137.65 | 122.06 | 75.55 |
| GFPT2-GLUTAMINE-FRUCTOSE-6-PHOSPHATE TRANSAMINASE 2 | 9 | 10.34 | 7.73 | 16.22 | 13.09 | 3.94 | 46.75 | 46.75 | 50.36 | 53.94 |
| HSPA6-HEAT SHOCK 70kDa PROTEIN 6 | 4.47 | 5.46 | 2.75 | 6.82 | 3.86 | 110.41 | 124.92 | 55.64 | 82.40 | 125.93 |
| SCARF2-SCAVENGER RECEPTOR CLASS F, MEMBER 2 | 2.36 | 4.47 | 4.82 | 5.78 | 6.06 | 2.50 | 4.50 | 5.93 | 2.98 | 4.66 |
| SNAI1-SNAIL HOMOLOG 1 (DROSOPHILA) | 12.21 | 3.68 | 7.89 | 2.69 | 9.19 | 8.17 | 8.19 | 6.02 | 5.42 | 6.15 |
| TP53BP2-TUMOR PROTEIN p53 BINDING PROTEIN, 2 | 2.33 | 3.18 | 2.66 | 5.46 | 2.35 | 2.13 | 2.69 | 1.97 | 2.58 | 3.21 |

FIG. 1

DRAMATIC PHENOTYPE CHANGES ASSOCIATED WITH EXPRESSION OF BARX1 IN NCI-N87 GC CELLS
EMPTY-VECTOR TRANSFECTED
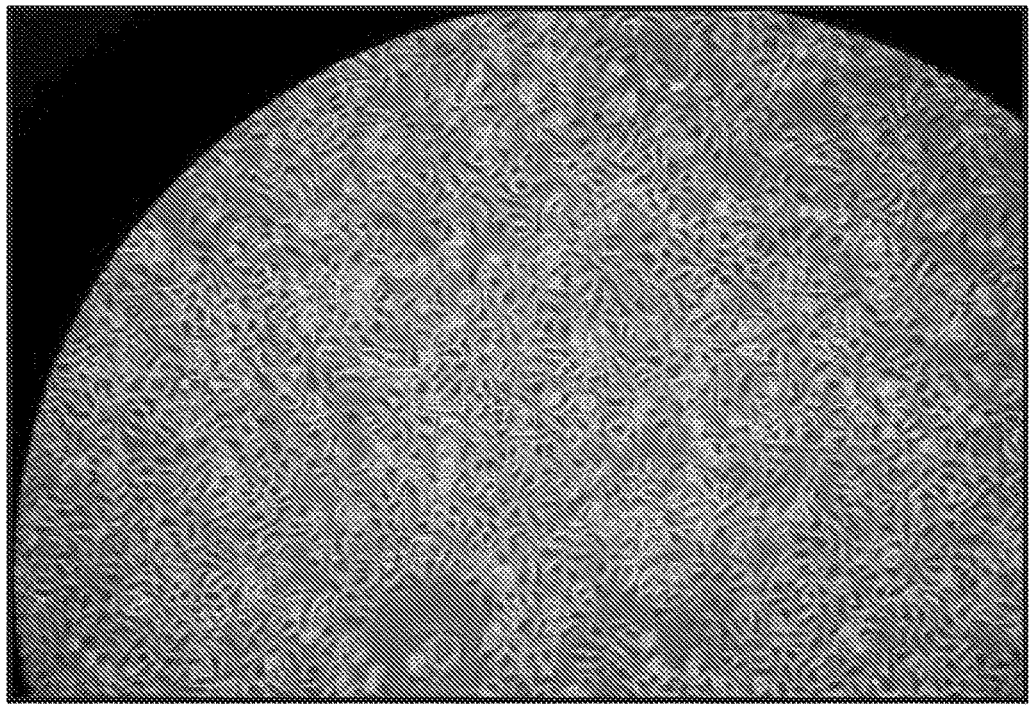
BARX1 VECTOR TRANSFECTED
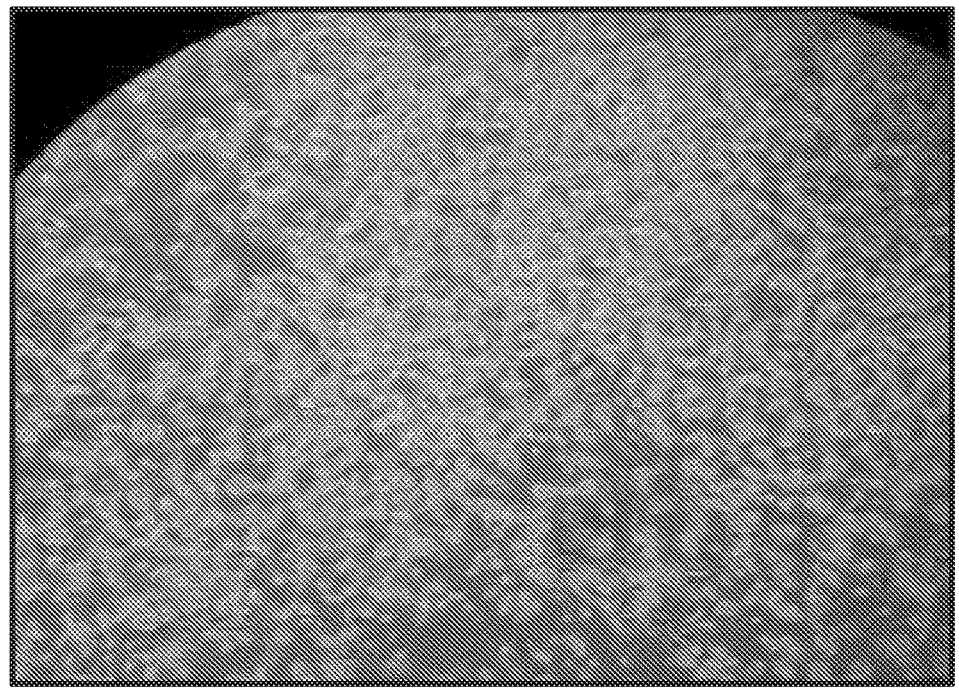
FIG. 4

EXPRESSION OF BARX1 IN GC CELLS: NCI-N87
EMPTY-VECTOR TRANSFECTED
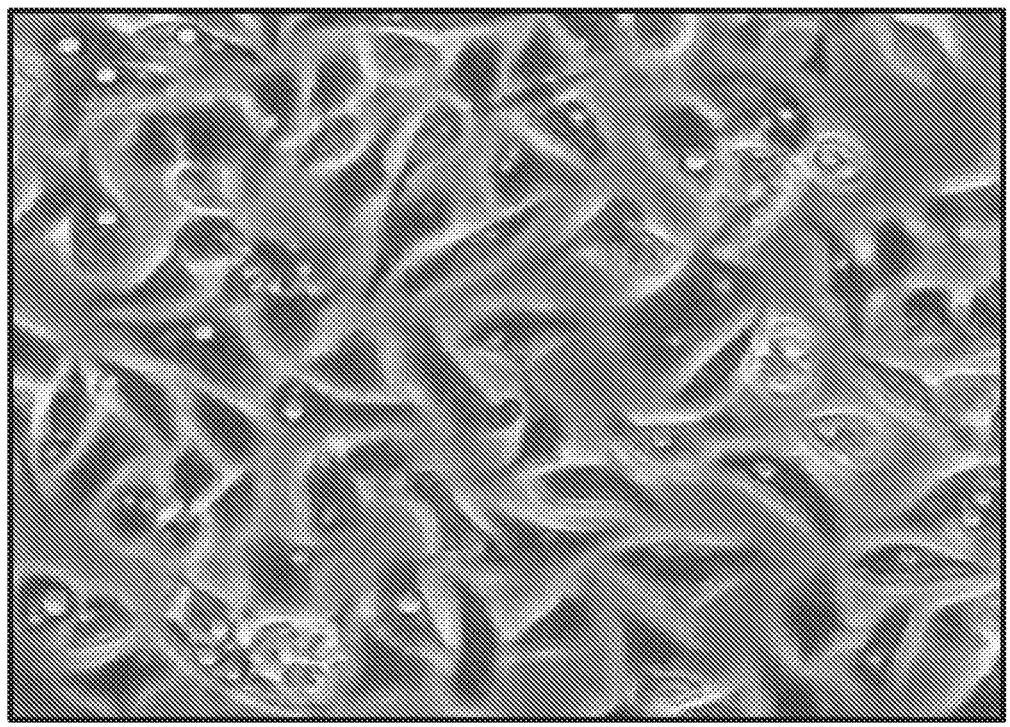
BARX1 VECTOR TRANSFECTED
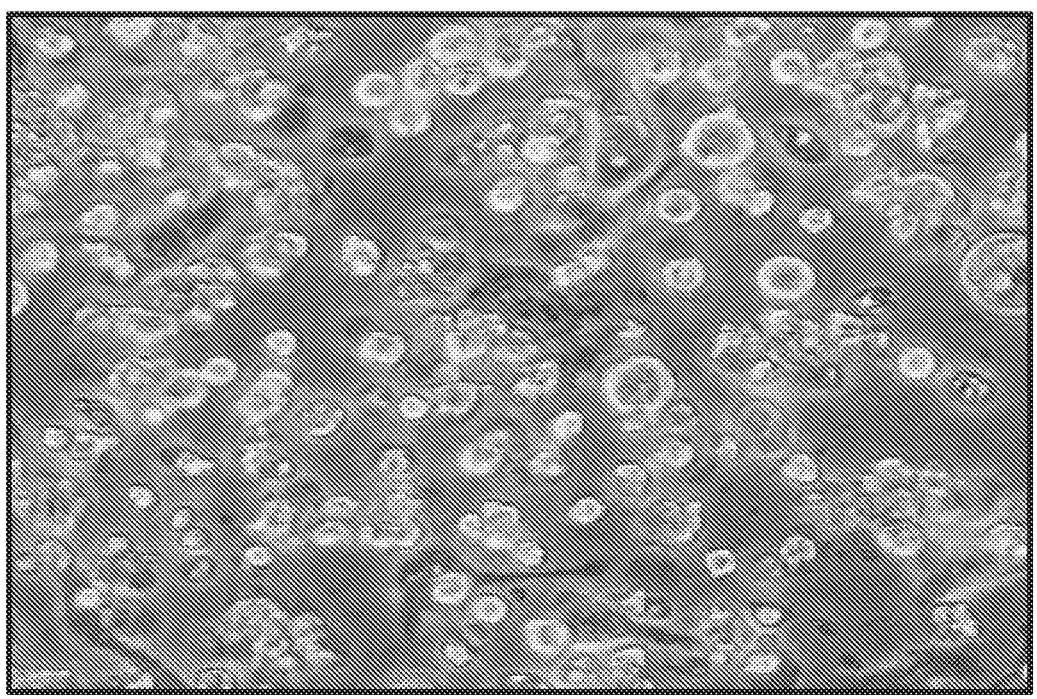
FIG. 5

OVEREXPRESSION OF Barx1 CAUSES APOPTOSIS
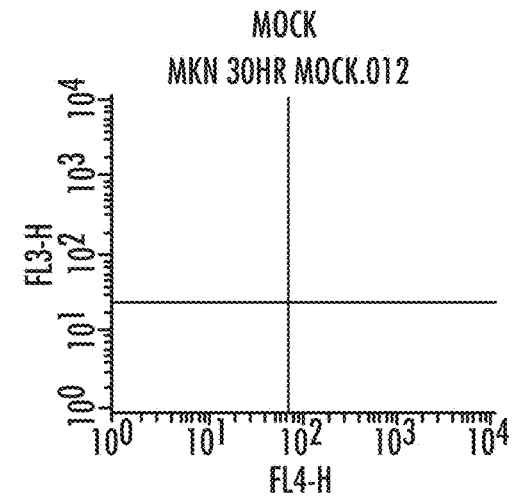
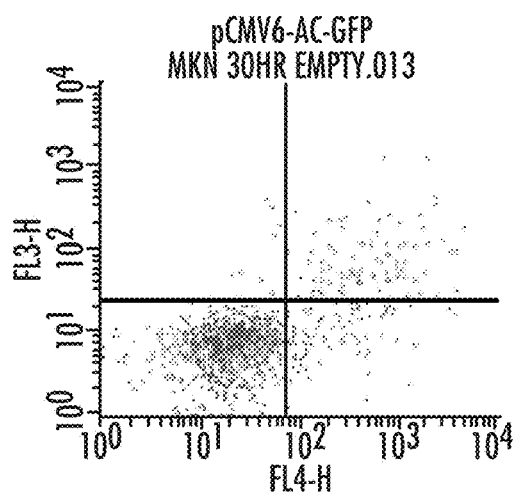
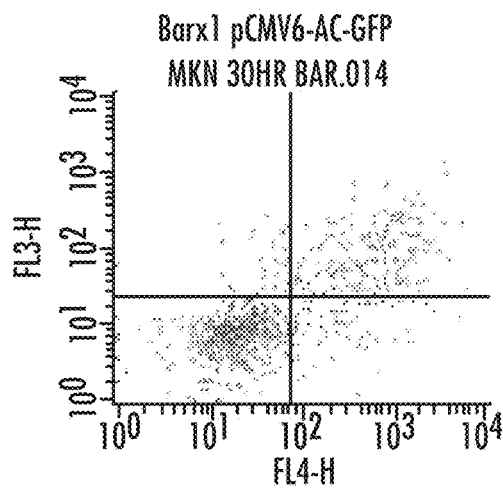
FIG. 15

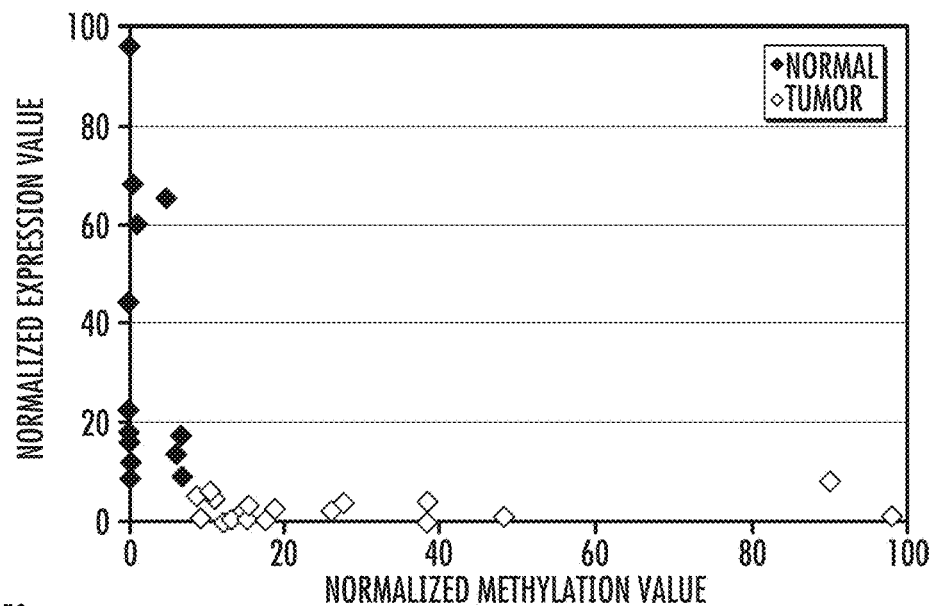
FIG. 18
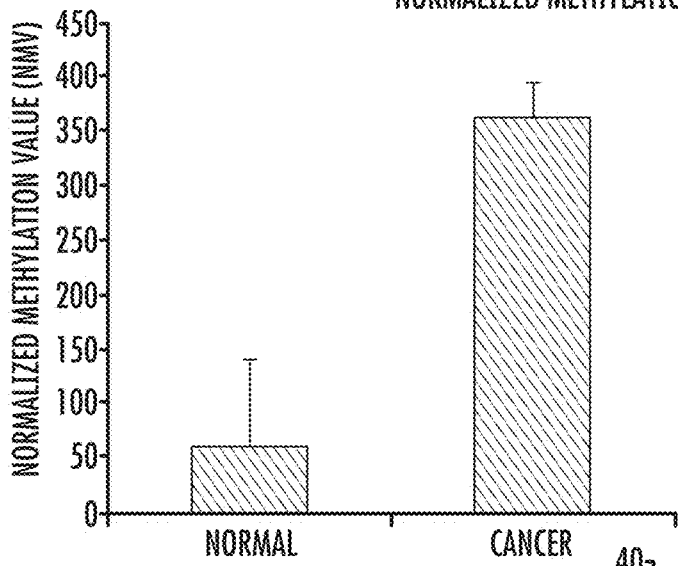
FIG. 19
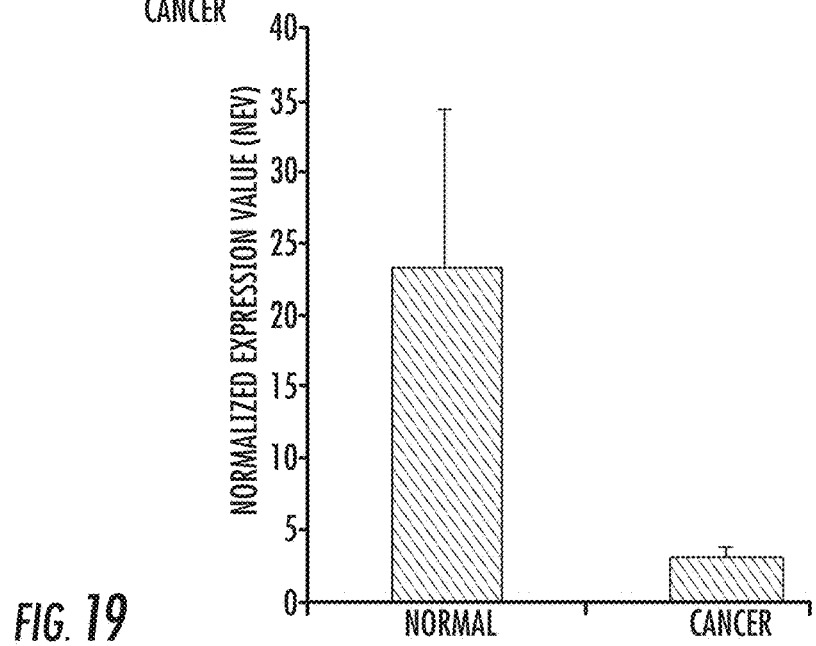

METHODS AND COMPOSITIONS FOR DIAGNOSING AND TREATING GASTRIC CANCER

CROSS-REFERENCE TO RELATED APPLICATIONS

This application is a 35 U.S.C. § 371 U.S. national entry of International Application PCT/US2013/071935, having an international filing date of Nov. 26, 2013, which claims the benefit of U.S. Provisional Application No. 61/729,772, filed Nov. 26, 2012, the content of each of the aforementioned applications is herein incorporated by reference in their entirety.

STATEMENT OF GOVERNMENTAL INTEREST

This invention was made with government support under grant no. NIH DK 087454 awarded by the National Institutes of Health. The government has certain rights in the invention.

FIELD OF THE INVENTION

The present invention relates to the field of gastric cancer. More specifically, the present invention provides methods and compositions for diagnosing and treating gastric cancer.

BACKGROUND OF THE INVENTION

Gastric cancer (GC), a disease with a very poor prognosis, is the second leading cause of cancer-related deaths worldwide. The poor prognosis of this cancer, due largely to delayed diagnosis, would be greatly improved by identification of biomarkers to stratify risk and accelerate diagnosis. Although few studies have identified genetic and epigenetic alterations to be involved in gastric carcinogenesis, the molecular pathogenesis of this disease remains incompletely understood, and largely unexplored.

SUMMARY OF THE INVENTION

The present invention is based, at least in part, on the discovery biomarkers for gastric cancer. Using a microarray-based genome-wide search, the present inventors identified several epigenetic targets in GC including tight junction protein claudin-11 (CLDN11), the transcription factor BarH-like homeobox (BARX1), basonuclin1 (BNC1), Coagulation factor C homolog (COCH), filamin C gamma (FLNC), cytoglobin B (CYGB), glutamine-fructose-6-phospahe-transaminase-2 (GFPT2), heat-shock-70 kDa protein-6 (HSPA6), snail homolog 1 (SNAL1), skin calmodulin-related factor (SCARF), and tumor protein p53 binding protein 2 (TP53BP2).

Accordingly, in one aspect, the present invention provides methods and compositions having utility for diagnostic, prognostic and therapeutic monitoring of gastric cancer. In a specific embodiment, a method for diagnosing gastric cancer or a likelihood thereof in a patient comprises the steps of (a) providing a sample from the patient; (b) measuring the methylation levels of one or more biomarkers in the sample collected from the patient; and (c) predicting gastric cancer in the patient if the biomarkers are hypermethylated. In a more specific embodiment, the one or more biomarkers comprises tight junction protein claudin-11 (CLDN11), the transcription factor BarH-like homeobox (BARX1), basonuclin1 (BNC1), Coagulation factor C homolog (COCH), filamin C gamma (FLNC), cytoglobin B (CYGB), glutamine-fructose-6-phospahe-transaminase-2 (GFPT2), heat-shock-70 kDa protein-6 (HSPA6), snail homolog 1 (SNAL1), skin calmodulin-related factor (SCARF), and tumor protein p53 binding protein 2 (TP53BP2). In a particular embodiment, the one or more biomarkers comprises BARX1. In a further embodiment, the one or more biomarkers comprises CLDN11. In certain embodiments, the sample is a blood or serum sample.

In another embodiment, a method for determining the risk of developing gastric cancer in a patient comprises the steps of (a) providing a sample from the patient; (b) measuring the methylation levels of a panel of biomarkers in the sample collected from the patient, wherein the panel of biomarkers comprises BARX1 and CLDN11; and (c) determining that the patient is at risk for developing gastric cancer if the biomarkers are hypermethylated. In a more specific embodiment, the panel of biomarkers further comprises one or more of CYGB, BNC1, COCH, FLNC, GFPT2, HSPA6, SNAL1, SCARF, and TP53BP2. In certain embodiments, the sample is a blood or serum sample.

In a further embodiment, a method for identifying a likelihood of gastric cancer in a patient comprises the steps of (a) providing a sample from the patient; (b) measuring the methylation levels of a panel of biomarkers in the sample collected from the patient, wherein the panel of biomarkers comprises one or more of BARX1, CYGB, CLDN11, BNC1, COCH, FLNC, GFPT2, HSPA6, SNAL1, SCARF, and TP53BP2; and (c) identifying the patient as likely to develop gastric cancer if the biomarkers are hypermethylated. In certain embodiments, the sample is a blood or serum sample.

In yet another embodiment, a method for diagnosing gastric cancer or a likelihood thereof in a patient comprises the steps of (a) providing a blood sample from the patient; (b) measuring the methylation levels of a panel of biomarkers in the sample collected from the patient, wherein the panel of biomarkers comprises one or more of BARX1, CYGB, CLDN11, BNC1, COCH, FLNC, GFPT2, HSPA6, SNAL1, SCARF, and TP53BP2; and (c) comparing the methylation levels of the one or more biomarkers with predefined methylation levels of the same biomarkers that correlate to a patient having gastric cancer and predefined methylation levels of the same biomarkers that correlate to a patient not having gastric cancer, wherein a correlation to one of the predefined methylation levels provides the prediction. In a specific embodiment, the panel of biomarkers comprises BARX1. In another specific embodiment, the panel of biomarkers further comprises CLDN11.

In another embodiment, a method for identifying gastric cancer in a patient comprises the steps of (a) obtaining nucleic acid from a sample taken from the patient, wherein the sample is from a specimen selected from the group consisting of tissue specimen, biopsy specimen, a surgical specimen, blood, plasma, serum, saliva, and a cytological specimen; (b) performing bisulfate modification to the nucleic acid in step (a); (c) performing quantitative methylation specific PCR (qMSP) on bilsulfite modified nucleic acid from step (b) using primers specific for the promoter region of one or more genes of interest, wherein the one or more genes of interest are selected from the group consisting of BARX1, CYGB, CLDN11, BNC1, COCH, FLNC, GFPT2, HSPA6, SNAL1, SCARF, and TP53BP2; (d) determining the promoter methylation level of the promoter regions of the one or more genes of interest in the nucleic acid from the sample of the patient; (e) providing a reference, non-neoplastic sample, wherein the reference, non-neoplastic sample is from a specimen selected from the consisting of tissue specimen, biopsy specimen, a surgical specimen, blood, plasma, serum, and a cytological specimen; (f) comparing the level of promoter methylation of the one or more genes of interest from the sample of the patient, to the level of promoter methylation of the one or more genes in a reference, non-neoplastic sample; and (g) identifying the patient as having gastric cancer when the level of methylation of the promoter region of one or more genes of interest in the sample of the patient, is increased relative to the methylation of the promoter region of the one or more genes of interest in a reference, non-neoplastic sample indicating epigenetic silencing of the one or more genes of interest. In certain embodiments, the method can further comprise step (h) administering a chemotherapeutic treatment regimen specific for gastric cancer to the patient.

In one embodiment, the epigenetic silencing of at least two genes is detected. In another embodiment, the epigenetic silencing of at least three genes is detected. In yet another embodiment, the epigenetic silencing of at least four genes is detected. In a further embodiment, the epigenetic silencing of at least five genes is detected.

In a specific embodiment, a method for determining the gastric cancer status in a patient comprises the steps of (a) providing a sample from the patient; (b) measuring the methylation levels of a panel of biomarkers in the sample collected from the patient, wherein the panel of biomarkers comprises one or more of BARX1, CYGB, CLDN11, BNC1, COCH, FLNC, GFPT2, HSPA6, SNAL1, SCARF, and TP53BP2; and (c) comparing the methylation levels of the panel of biomarkers with predefined methylation levels of the same panel of biomarkers that correlate to one or more gastric cancer statuses selected from the group consisting of having gastric cancer, not having gastric cancer, progressing gastric cancer, and regressing gastric cancer, wherein a correlation to one of the predefined methylation levels determines the gastric cancer status of the patient. In a more specific embodiment, the panel of biomarkers comprises BARX1. In a further embodiment, the panel of biomarkers further comprises CLDN11.

In yet another embodiment, a method for diagnosing gastric cancer in a patient comprises the steps of (a) providing a sample from the patient; (b) measuring the methylation levels BARX1 in the sample collected from the patient; and (c) diagnosing the patient as having gastric cancer if BARX1 is hypermethylated.

In another aspect, the present invention provides kits. In a specific embodiment, a diagnostic kit for determining gastric cancer status in a patient comprises (a) a substrate for collecting a biological sample from the patient; and (b) means for measuring the methylation levels of one or more biomarkers selected from the group consisting of BARX1, CYGB, CLDN11, BNC1, COCH, FLNC, GFPT2, HSPA6, SNAL1, SCARF, and TP53BP2. In a more specific embodiment, the means for measuring the methylation levels of one or more biomarkers are oligonucleotide primers specific for amplifying methylated regions of the biomarkers.

In other embodiments, a kit for assessing gastric cancer in a test sample containing gastric cancer cells or nucleic acids from gastric cancer cells comprises (a) a reagent that (i) modifies methylated cytosine residues but not non-methylated cytosine residues, or that (ii) modifies non-methylated cytosine residues but not methylated cytosine residues; (b) at least one pair of oligonucleotide primers that specifically hybridizes under amplification conditions to a region of a gene selected from the group consisting of BARX1, CYGB, CLDN11, BNC1, COCH, FLNC, GFPT2, HSPA6, SNAL1, SCARF, and TP53BP2, wherein the region is within about 1 kb of the gene's transcription start site; and (c) instructions for assessing gastric cancer using the reagents. In one embodiment, the kit comprises at least three pairs of primers. In another embodiment, the kit comprises at least four pairs of primers. In a further embodiment, the kit comprises at least five pairs of primers. In certain embodiments, the kit comprises at least a first and a second pair of oligonucleotide primers that specifically hybridizes under amplification conditions to a region of BARX1 and CLDN11.

BRIEF DESCRIPTION OF THE FIGURES

FIG. 1 is a list of genes hypermethylated and downregulated in all 5 gastric cancer cell lines vs. normal gastric epithelial cells.

FIG. 4 shows the dramatic phenotype changes associated with expression of BARX1 in NCI-N87 GC cells.

FIG. 5 shows the dramatic phenotype changes associated with expression of BARX1 in NCI-N87 GC cells.

FIG. 13. siRNA silencing of endogenous Barx1.

FIG. 14A. HEK293 cells transfected with Barx1 demonstrate morphological changes. Mock transfects pictured in the UL Panel, Barx1 transfects pictured in the UR panel.

FIG. 15. Induction of apoptosis following transfection (30 h) with Barx1 plasmid was examined using Annexin V-APC/7-AAD method. Preliminary data suggests that those cells transfected with Barx1, vs. their pCMV6-AC-GFP (no insert) counterparts, undergo rapid rates of apoptosis. The data demonstrate that after 30 h of expressing the gene, secondary necrosis was 16% higher in Barx1 expressing cells than in no-insert counterparts.

FIG. 18. 2D scatterplot of claudin-11 NEV vs. NMV in clinical specimens. A strong inverse relationship is seen between normalized expression values (NEV) and normalized methylation (NMV) values.

FIG. 19. Quantitative methylation-specific PCR (qMSP, left) for BARX1 methylation levels and qRT-PCR (right) for BARX1 mRNA expression levels in primary gastric tissues. N=18 normal gastric mucosae and 18 primary GCs.

DETAILED DESCRIPTION OF THE INVENTION

Figure 2:
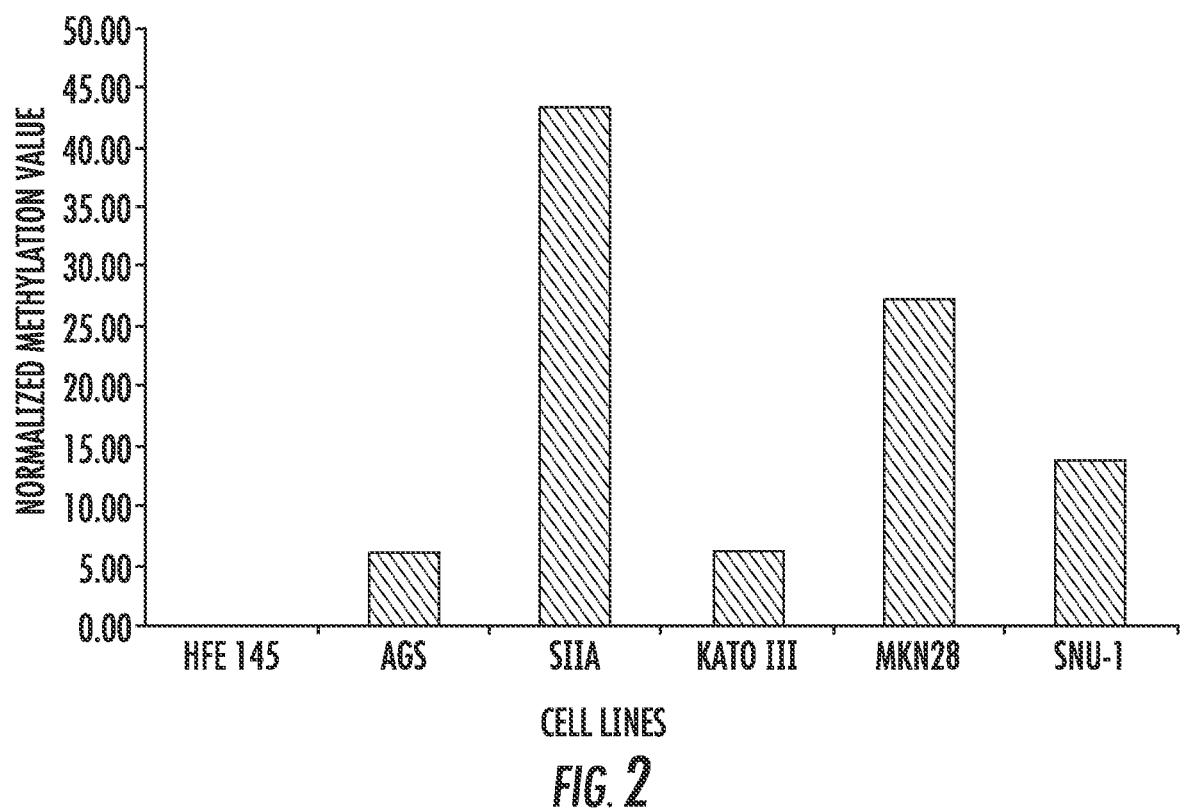
FIG. 2 is a graph showing qMSP results from BARX1 in the cell lines used for microarray experiments. qMSP confirms that all GC cell lines have high promoter methylation levels of Barx1, but no methylation in NGECs.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "comparing" refers to making an assessment of how the methylation status, proportion, level or cellular localization of one or more biomarkers in a sample from a patient relates to the methylation status, proportion, level or cellular localization of the corresponding one or more biomarkers in a standard or control sample. For example, "comparing" may refer to assessing whether the methylation status, proportion, level, or cellular localization of one or more biomarkers in a sample from a patient is the same as, more or less than, or different from the methylation status, proportion, level, or cellular localization of the corresponding one or more biomarkers in standard or control sample. More specifically, the term may refer to assessing whether the methylation status, proportion, level, or cellular localization of one or more biomarkers in a sample from a patient is the same as, more or less than, different from or otherwise corresponds (or not) to the methylation status, proportion, level, or cellular localization of predefined biomarker levels that correspond to, for example, a patient having gastric cancer, at risk for developing gastric cancer, not having gastric cancer, is responding to treatment for gastric cancer, is not responding to treatment for gastric cancer, is/is not likely to respond to a particular gastric cancer treatment, or having/not having another disease or condition. In a specific embodiment, the term "comparing" refers to assessing whether the methylation level of one or more biomarkers of the present invention in a sample from a patient is the same as, more or less than, different from other otherwise correspond (or not) to methylation levels of the same biomarkers in a control sample (e.g., predefined levels that correlate to uninfected individuals, standard gastric cancer levels, etc.).

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has gastric cancer. In specific embodiments, the parameter may comprise the methylation status or level of one or more biomarkers of the present invention. A particular set or pattern of methylation of one or more biomarkers may indicate that a patient has gastric cancer (i.e., correlates to a patient having gastric cancer) or is at risk of developing gastric cancer. In other embodiments, a particular set or pattern of methylation of one or more biomarkers may be correlated to a patient being unaffected. In certain embodiments, "indicating," or "correlating," as used according to the present invention, may be by any linear or non-linear method of quantifying the relationship between methylation levels of biomarkers to a standard, control or comparative value for the assessment of the diagnosis, prediction of gastric cancer or gastric cancer progression, assessment of efficacy of clinical treatment, identification of a patient that may respond to a particular treatment regime or pharmaceutical agent, monitoring of the progress of treatment, and in the context of a screening assay, for the identification of an anti-gastric cancer therapeutic.

The terms "patient," "individual," or "subject" are used interchangeably herein, and refer to a mammal, particularly, a human. The patient may have mild, intermediate or severe disease. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the methylation status or level of a biomarker(s) in a sample. In one embodiment, the terms refer to obtaining a patient sample and detecting the methylation status or level of one or more biomarkers in the sample. In another embodiment, the terms "measuring" and "determining" mean detecting the methylation status or level of one or more biomarkers in a patient sample. Measuring can be accomplished by methods known in the art and those further described herein including, but not limited to, quantitative polymerase chain reaction (PCR). The term "measuring" is also used interchangeably throughout with the term "detecting."

The term "methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a patient over time.

In particular embodiments, a biomarker would be unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, a biomarker would be hypermethylated in a sample from a patient having or at risk of gastric cancer, preferably at a methylation frequency of at least about 50%, at least about 60%, at least about 70%, at least about 75%, at least about 80%, at least about 85%, at least about 90%, at least about 95%, or about 100%.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including BARX1, CYGB, CLDN11, BNC1, COCH, FLNC, GFPT2, HSPA6, SNAL1, SCARF, and TP53BP2.

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) NUCLEIC ACIDS RES. 3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence.

One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of gastric cancer. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a blood sample. In another embodiment, a serum sample is used. In another embodiment, a sample comprises amniotic fluid. In yet another embodiment, a sample comprises amniotic fluid. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a gastric cancer treatment) on a patient. In yet another embodiment, a transcription rate, mRNA level, translation rate, protein level, biological activity, cellular characteristic or property, genotype, phenotype, etc. can be determined prior to, during, or after administering a therapy into a cell, organ, or patient. In a further embodiment, a "suitable control" or "appropriate control" is a predefined value, level, feature, characteristic, property, etc. A "suitable control" can be a methylation profile of one or more biomarkers of the present invention that correlates to gastric cancer, to which a patient sample can be compared. The patient sample can also be compared to a negative control, i.e., a methylation profile that correlates to not having gastric cancer.

II. Hypermethylated Biomarkers and Detection Thereof

The biomarkers of the present invention are differentially methylated in gastric cancer versus normal tissue. Such biomarkers can be used individually as diagnostic tool, or in combination as a biomarker panel. In particular embodiments, the biomarkers include BARX1, CYGB, CLDN11, BNC1, COCH, FLNC, GFPT2, HSPA6, SNAL1, SCARF, and TP53BP2. The sequences of these biomarkers are publicly available.

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease or condition (e.g., gastric cancer).

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease or condition (e.g., gastric cancer) and thus diagnose the onset, presence or status of the disease or condition.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al., 34(1) BIOTECHNIQUES 106-15 (2003); Deiman B, et al., 20(2) MOL. BIOTECHNOL. 163-79 (2002); and Gibson et al., 6 GENOME RESEARCH 995-1001 (1996). Amplifications may be monitored in "real time."

Additional methods for detecting DNA methylation can involve genomic sequencing before and after treatment of the DNA with bisulfite. See, e.g., Frommer et al., 89 PROC. NATL. ACAD. SCI. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See, e.g., Xiong & Laird, 25 NUCLEIC ACIDS RES. 2532-34 (1997); and Sadri & Hornsby, 24 NUCL. ACIDS RES. 5058-59 (1996).

In some embodiments, a MethyLight assay is used alone or in combination with other methods to detect DNA methylation. See, Eads et al., 59 CANCER RES. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of an unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 NUCLEIC ACIDS RES. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 PROC. NATL. ACAD. SCI. USA 9821-26, (1996); and U.S. Pat. No. 5,786,146.

Additional methylation detection methods include, but are not limited to, methylated CpG island amplification (see, Toyota et al., 59 CANCER RES. 2307-12 (1999)) and those methods described in, e.g., U.S. Pat. Nos. 7,553,627; 6,331, 393; U.S. patent Ser. No. 12/476,981; U.S. Patent Publication No. 2005/0069879; Rein, et al., 26(10) NUCLEIC ACIDS RES. 2255-64 (1998); and Olek et al., 17(3) NAT. GENET. 275-6 (1997).

III. Determination of a Patient's Gastric Cancer Status

The present invention relates to the use of biomarkers to detect or predict gastric cancer. More specifically, the biomarkers of the present invention can be used in diagnostic tests to determine, qualify, and/or assess gastric cancer status, for example, to diagnose or predict gastric cancer, in an individual, subject or patient. More specifically, the biomarkers to be detected in diagnosing gastric cancer include, but are not limited to, tight junction protein claudin-11 (CLDN11), the transcription factor BarH-like homeobox (BARX1), basonuclin1 (BNC1), Coagulation factor C homolog (COCH), filamin C gamma (FLNC), cytoglobin B (CYGB), glutamine-fructose-6-phospahe-transaminase-2 (GFPT2), heat-shock-70 kDa protein-6 (HSPA6), snail homolog 1 (SNAL1), skin calmodulin-related factor (SCARF), and tumor protein p53 binding protein 2 (TP53BP2). Other biomarkers known in the relevant art may be used in combination with the biomarkers described herein.

A. Biomarker Panels

The biomarkers of the present invention can be used in diagnostic tests to assess, determine, and/or qualify (used interchangeably herein) gastric cancer status in a patient. The phrase "gastric cancer status" includes any distinguishable manifestation of the disease, including non-disease. For example, gastric cancer status includes, without limitation, the presence or absence of gastric cancer in a patient), the risk of developing gastric cancer, the stage of gastric cancer, the progress of gastric cancer (e.g., progress of gastric cancer over time) and the effectiveness or response to treatment of gastric cancer (e.g., clinical follow up and surveillance of gastric cancer after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different gastric cancer statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated in UI (or NC) and gastric cancer, and, therefore, are useful in aiding in the determination of gastric cancer status. In certain embodiments, the biomarkers are measured in a patient sample using the methods described herein and compared, for example, to predefined biomarker levels and correlated to gastric cancer status. In particular embodiments, the measurement(s) may then be compared with a relevant diagnostic amount(s), cut-off(s), or multivariate model scores that distinguish a positive gastric cancer status from a negative gastric cancer status. The diagnostic amount(s) represents a measured amount of a hypermethylated biomarker(s) above which or below which a patient is classified as having a particular gastric cancer status. For example, if the biomarker(s) is/are hypermethylated compared to normal during gastric cancer, then a measured amount(s) above the diagnostic cutoff(s) provides a diagnosis of gastric cancer. Alternatively, if the biomarker(s) is/are hypomethylated in a patient, then a measured amount(s) at or below the diagnostic cutoff(s) provides a diagnosis of non-gastric cancer. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from patients with the different gastric cancer statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to diagnose gastric cancer, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Developing Gastric Cancer

In a specific embodiment, the present invention provides methods for determining the risk of developing gastric cancer in a patient. Biomarker methylation percentages, amounts or patterns are characteristic of various risk states, e.g., high, medium or low. The risk of developing gastric cancer is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Determining Gastric Cancer Severity

In another embodiment, the present invention provides methods for determining the severity of gastric cancer in a patient. A particular stage or severity of gastric cancer may have a characteristic level of hypermethylation of a biomarker or relative hypermethylated levels of a set of biomarkers (a pattern). The severity of gastric cancer can be determined by measuring the methylation status of the relevant biomarkers and then either submitting them to a classification algorithm or comparing them with a reference amount, i.e., a predefined methylation level or pattern of methylated biomarkers that is associated with the particular stage.

D. Determining Gastric Cancer Prognosis

In one embodiment, the present invention provides methods for determining the course of gastric cancer in a patient. gastric cancer course refers to changes in gastric cancer status over time, including gastric cancer progression (worsening) and gastric cancer regression (improvement). Over time, the amount or relative amount (e.g., the pattern) of hypermethylation of the biomarkers changes. For example, hypermethylation of biomarker "X" and "Y" may be increased with gastric cancer. Therefore, the trend of these biomarkers, either increased or decreased methylation over time toward gastric cancer or non-gastric cancer indicates the course of the disease. Accordingly, this method involves measuring the methylation level or status of one or more biomarkers in a patient at least two different time points, e.g., a first time and a second time, and comparing the change, if any. The course of gastric cancer is determined based on these comparisons.

E. Patient Management

In certain embodiments of the methods of qualifying gastric cancer status, the methods further comprise managing patient treatment based on the status. Such management includes the actions of the physician or clinician subsequent to determining gastric cancer status. For example, if a physician makes a diagnosis or prognosis of gastric cancer, then a certain regime of monitoring would follow. An assessment of the course of gastric cancer using the methods of the present invention may then require a certain gastric cancer therapy regimen. Alternatively, a diagnosis of non-gastric cancer might be followed with further testing to determine a specific disease that the patient might be suffering from. Also, further tests may be called for if the diagnostic test gives an inconclusive result on gastric cancer status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-gastric cancer profile. Therefore, one can follow the course of the methylation status of one or more biomarkers in the patient during the course of treatment. Accordingly, this method involves measuring methylation levels of one or more biomarkers in a patient receiving drug therapy, and correlating the levels with the gastric cancer status of the patient (e.g., by comparison to predefined methylation levels of the biomarkers that correspond to different gastric cancer statuses). One embodiment of this method involves determining the methylation levels of one or more biomarkers at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward gastric cancer indications.

G. Generation of Classification Algorithms for Qualifying Gastric Cancer Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

H. Kits for the Detection of Gastric Cancer Biomarker Biomarkers

In another aspect, the present invention provides kits for qualifying gastric cancer status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Reagents for detection of methylation include, e.g., sodium bisulfite, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region of a biomarker of the present invention including BARX1, CYGB, CLDN11, BNC1, COCH, FLNC, GFPT2, HSPA6, SNAL1, SCARF, and TP53BP2. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including BARX1, CYGB, CLDN11, BNC1, COCH, FLNC, GFPT2, HSPA6, SNAL1, SCARF, and TP53BP2.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of a biomarker of the present invention including BARX1, CYGB, CLDN11, BNC1, COCH, FLNC, GFPT2, HSPA6, SNAL1, SCARF, and TP53BP2.

In some embodiments, the kits comprise a methylation binding moiety and one or more polynucleotides to quantify the number of copies of at least a portion of a DNA region of a biomarker of the present invention including BARX1, CYGB, CLDN11, BNC1, COCH, FLNC, GFPT2, HSPA6, SNAL1, SCARF, and TP53BP2. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Identification of Candidate Tumor Suppressor Genes

The goal of the present example was to understand, and identify the molecular pathways important in the pathogenesis of GC, and in particular, to identify targets for its detection and therapy In a specific aim, the present inventors sough to identify candidate TSGs that are hypermethylated in the promoter region, and coordinately downregulated in their mRNA expression in GC cells.

CpG island Methylation and mRNA Expression Microarrays. Microarray-based CpG island methylation analysis (Agilent) and mRNA expression arrays (Illumina) were used. Immortalized normal gastric epithelial cell line HFE145 and gastric cancer cell lines SNU-1, zKATOIII, MKN28, SIIA and AGS were used. In Microarray-based CpG Island Methylation Analysis (MCAM), the methylated DNA fragments were first enriched. Then, the enriched methylated DNA fragments were used as probe for the CpG island oligonucleotide microarray.

To identify candidate TSGs that are hypermethylated in the promoter region, and coordinately downregulated in their mRNA expression in GC cells, results of CpG island arrays were correlated with the mRNA array results. The list of genes hypermethylated and downregulated in all 5 gastric cancer cell lines vs. normal gastric epithelial cells are shown in FIG. 1

Figure 12:
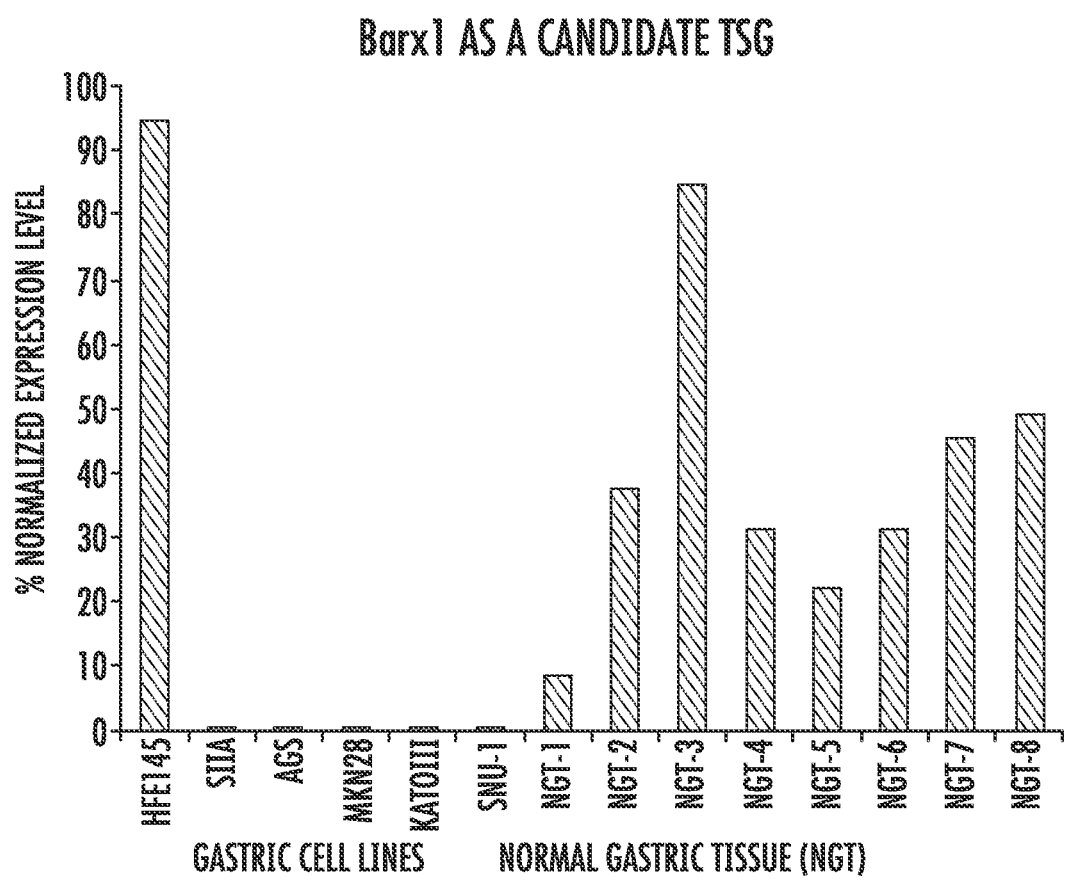
FIG. 12. Barx1 Expression Levels in Cells and Tissue. HFE145 and Normal Gastric Tissues expressed very high levels of Barx1, while all five cancer cell lines examined had very low or undetectable Barx1 levels.
Figure 13A:
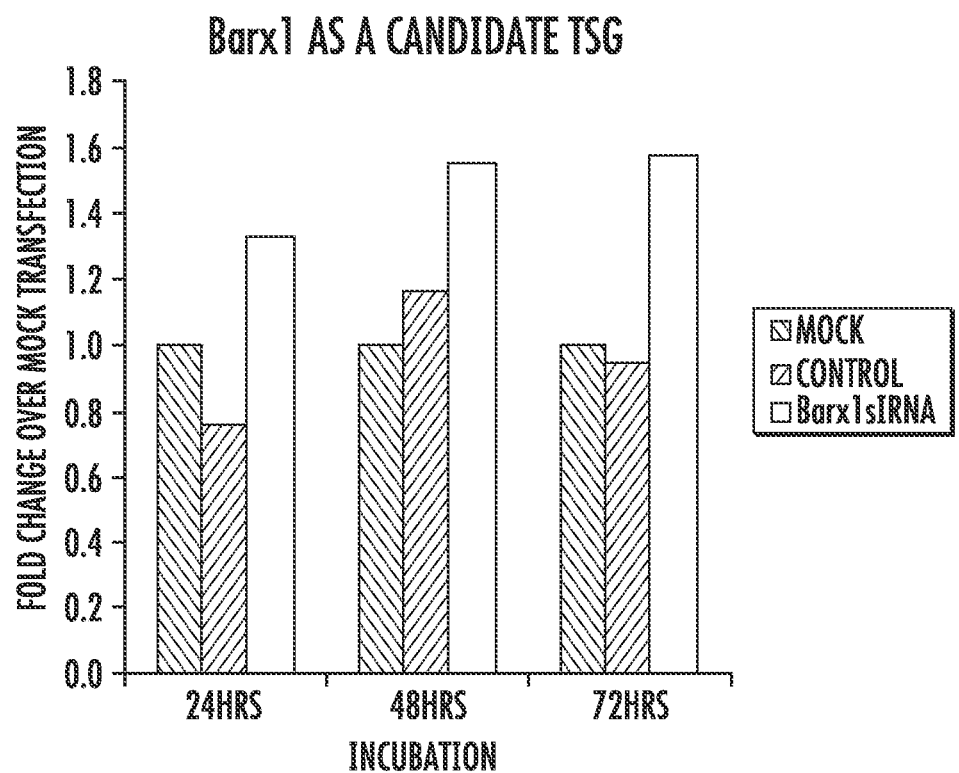
FIG. 13A. Barrx1 knockdown in HFE145 cells and WST-1 assay. Results indicated that suppression of endogenous Barx1 leads to increased cell proliferation.
Figure 13B:
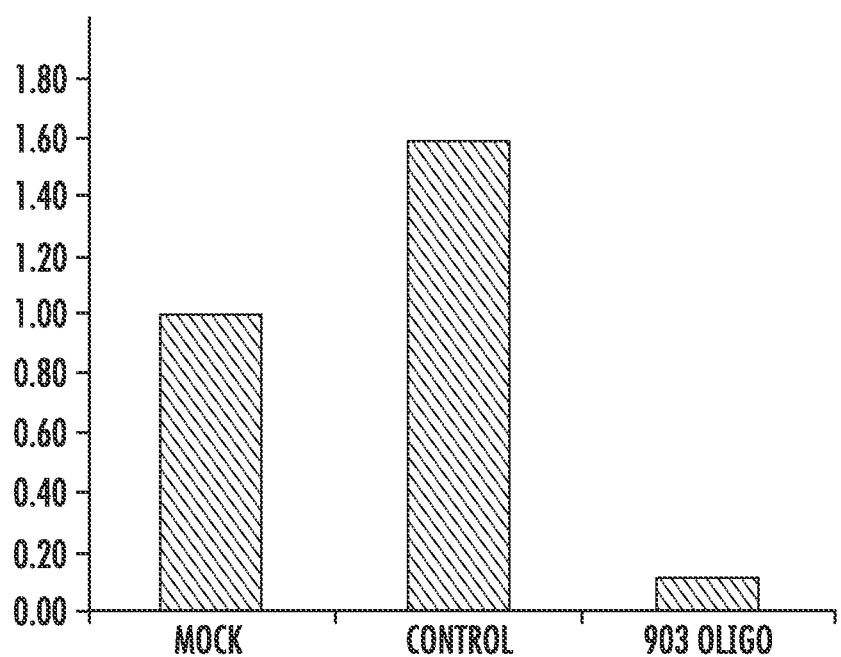
FIG. 13B. RT-PCR of BARX1 siRNA Knockdown Experiment. PCR confirms that siRNAs targeting Barx1 successfully silence expression of the transcript.
Figure 14:
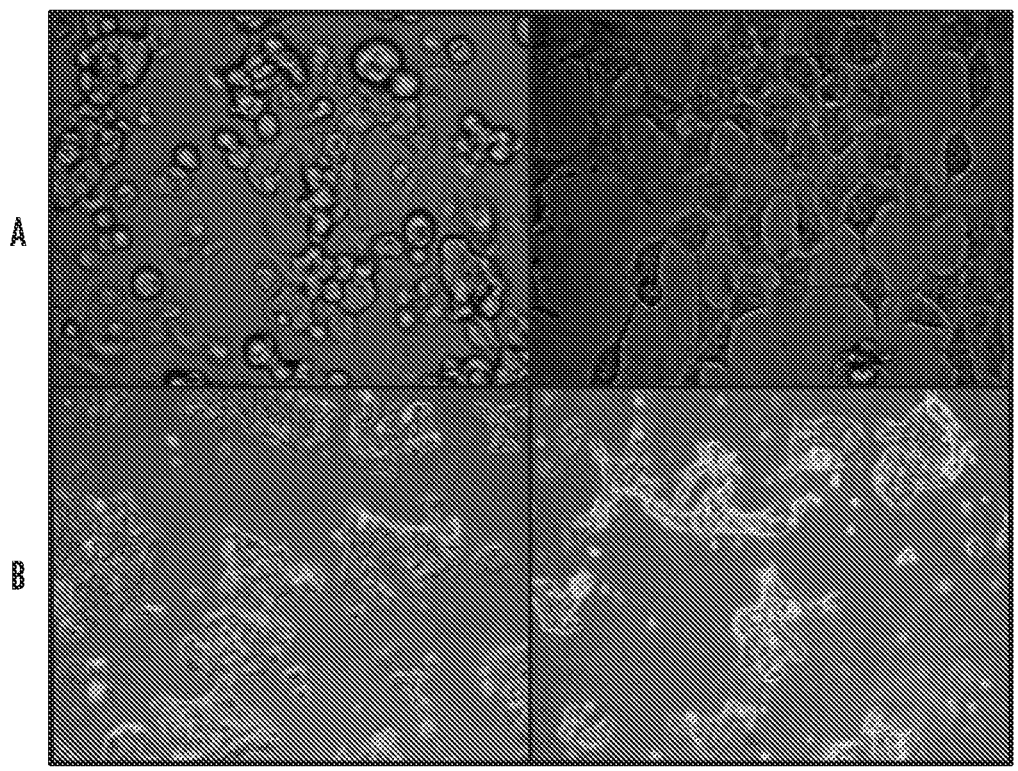
FIG. 14 B. MKN28 cells also demonstrate strong changes. 3 Days after transfection massive cell death has been observed. Barx1 transfects at t=0D LL Panel, t=3D Barx1 transfects LR Panel.
Figure 16:
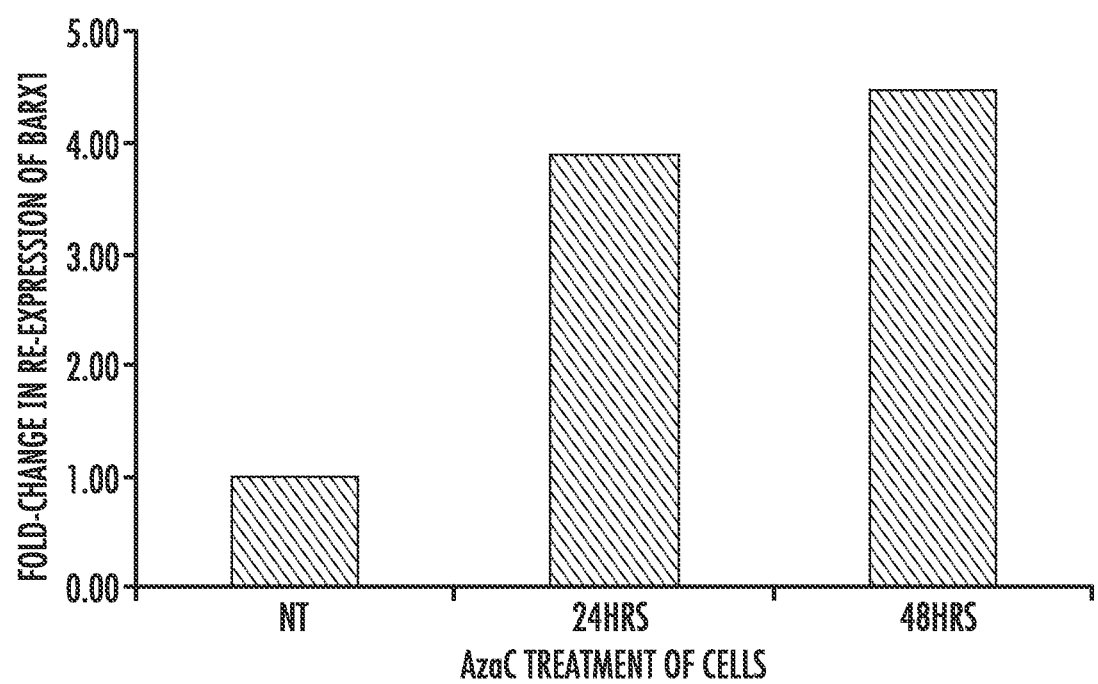
FIG. 16 is a graph showing BARX mRNA re-expression in AGS after 5-AzaC treatment.

Validation of Microarray Data. As with methylation arrays, qMSP confirms that all GC cell lines have high promoter methylation levels of Barx1, but no methylation in NGECs. See FIG. 2. As shown in FIG. 12, HFE145 and NGTs expressed very high levels of Barx1, while all five cancer cell lines tested had very low or undetectable Barx1 levels. Further, as shown in FIG. 16, the restoration of Barx1 expression after 5-Aza-dC treatment supports the hypothesis that Barx1 is silenced by promoter hypermethylation in GC cells.

Figure 3:
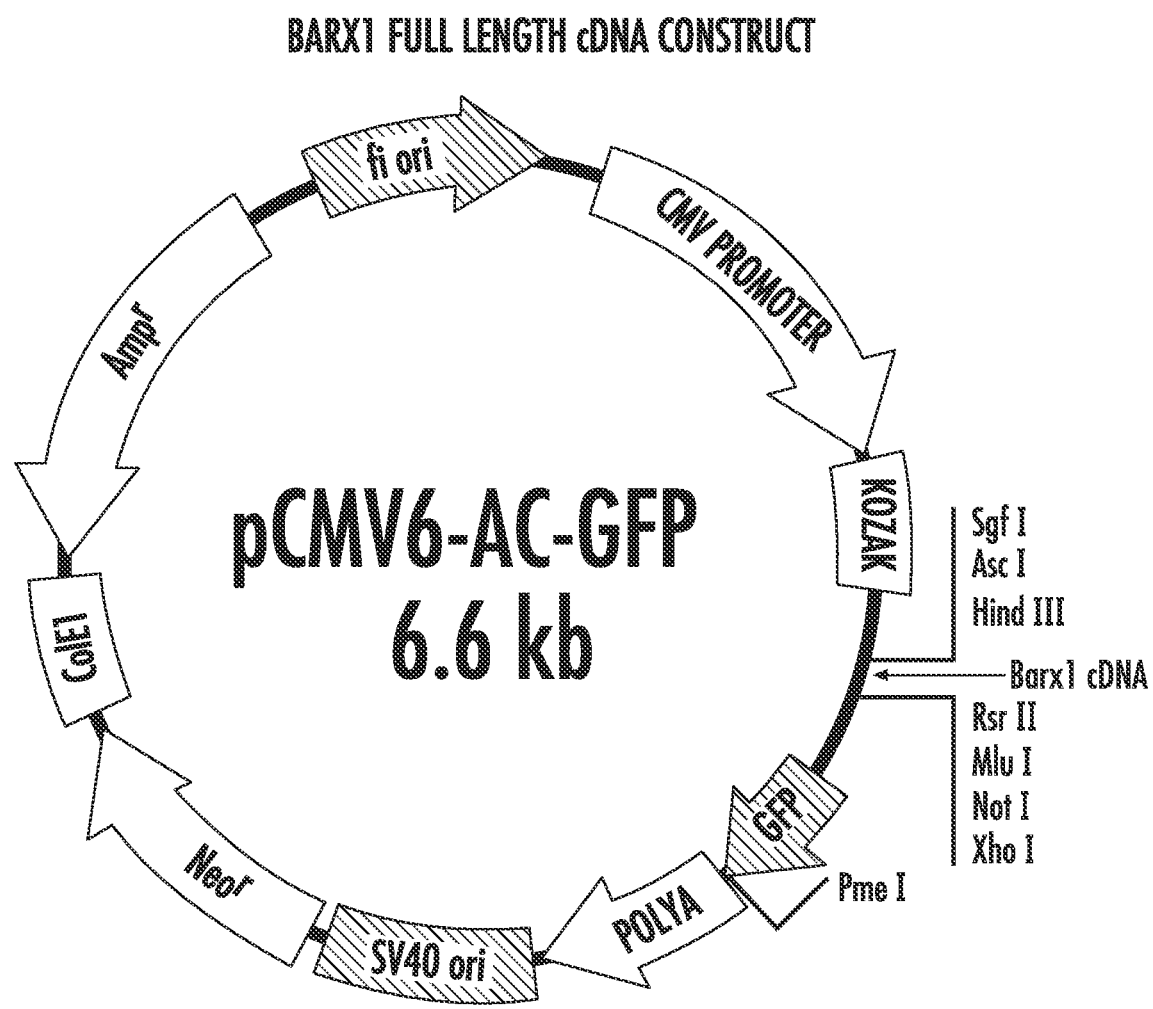
FIG. 3 is a plasmid map showing the Barx1 full length cDNA construct.

To understand possible functional implications of Barx1 in gastric cancer, Barx1 was over-expressed in Barx1 negative GC cell lines (obtained mammalian expression vectors expressing full length, wild-type Barx1), and various functional studies were carried out using these transfected cells. See FIG. 3.

Figure 6:
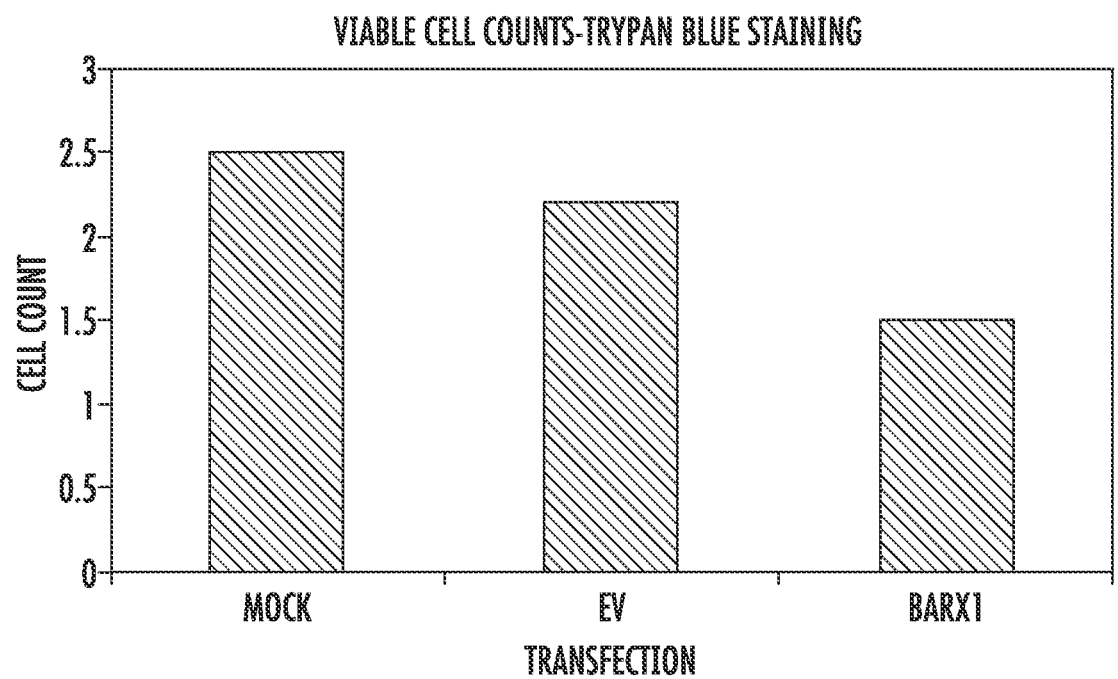
FIG. 6 is a graph showing that viable cell count was reduced in Barx1 transfected cells.

Transfection of BARX1 cDNA into GC cells. As shown in FIG. 4, dramatic phenotype changes were associated with expression of BARX1 in NCI-N87 GC cells. Dramatic phenotype changes were also associated with expression of BARX1 in NCI-N87 GC cells (FIG. 5). Viable cell count was reduced in Barx1 transfected cells (FIG. 6). These experiments were repeated in NCI-N87, as well as in AGS cells, and consistent results were obtained.

Figure 7:
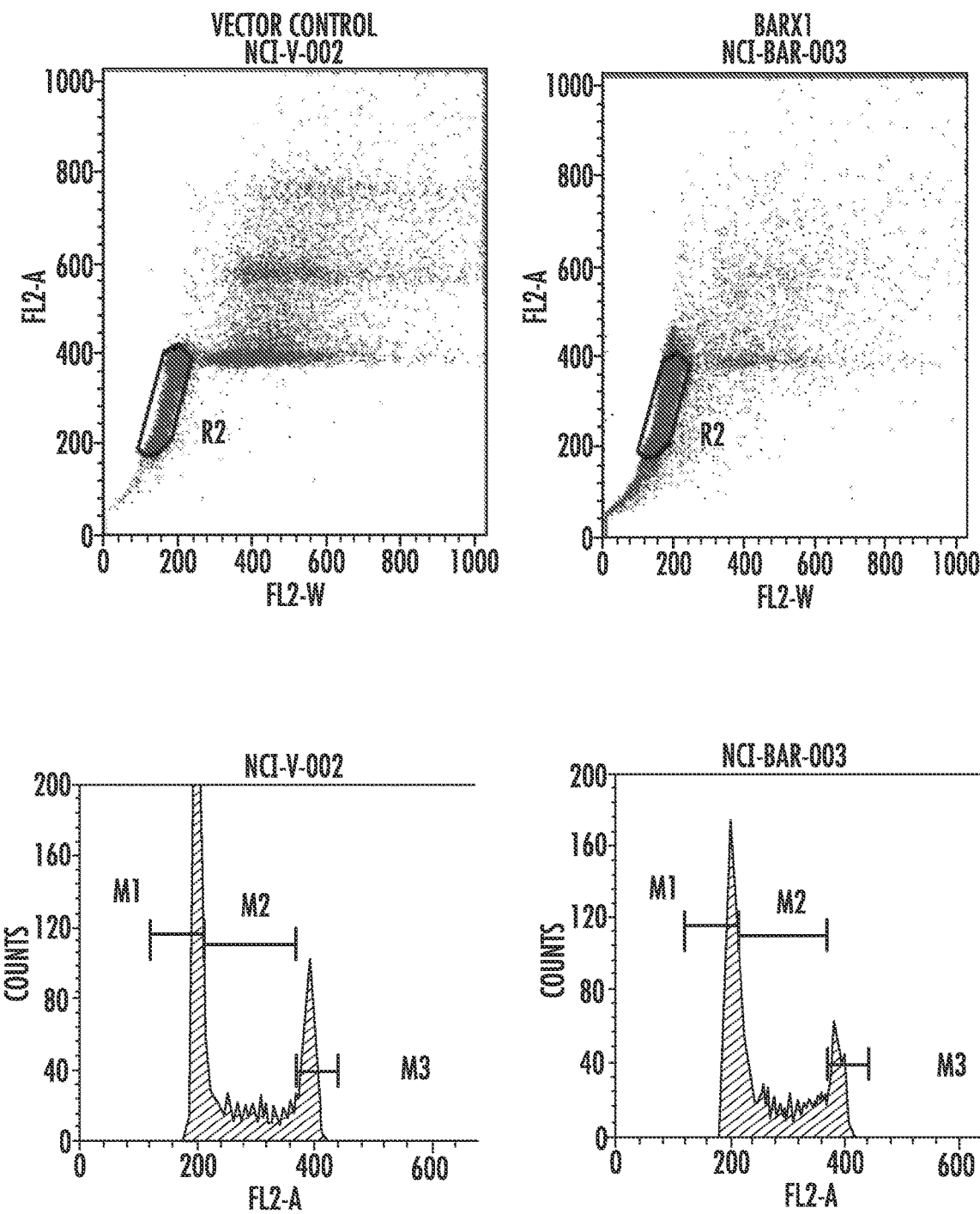
FIGS. 7-9 show results from cell cycle analysis of NCI-N87 and AGS cells.
Figure 8:
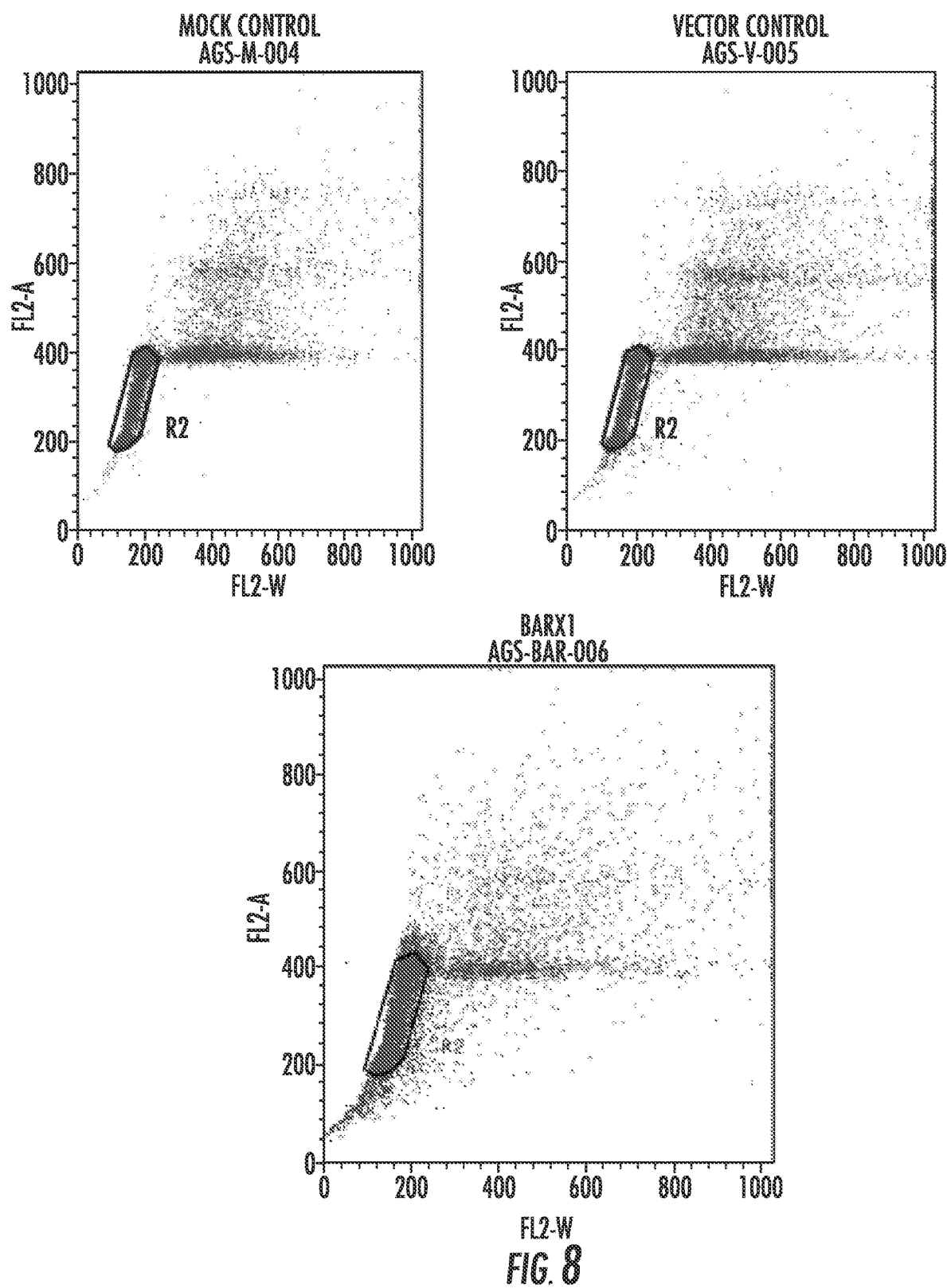
Figure 9:
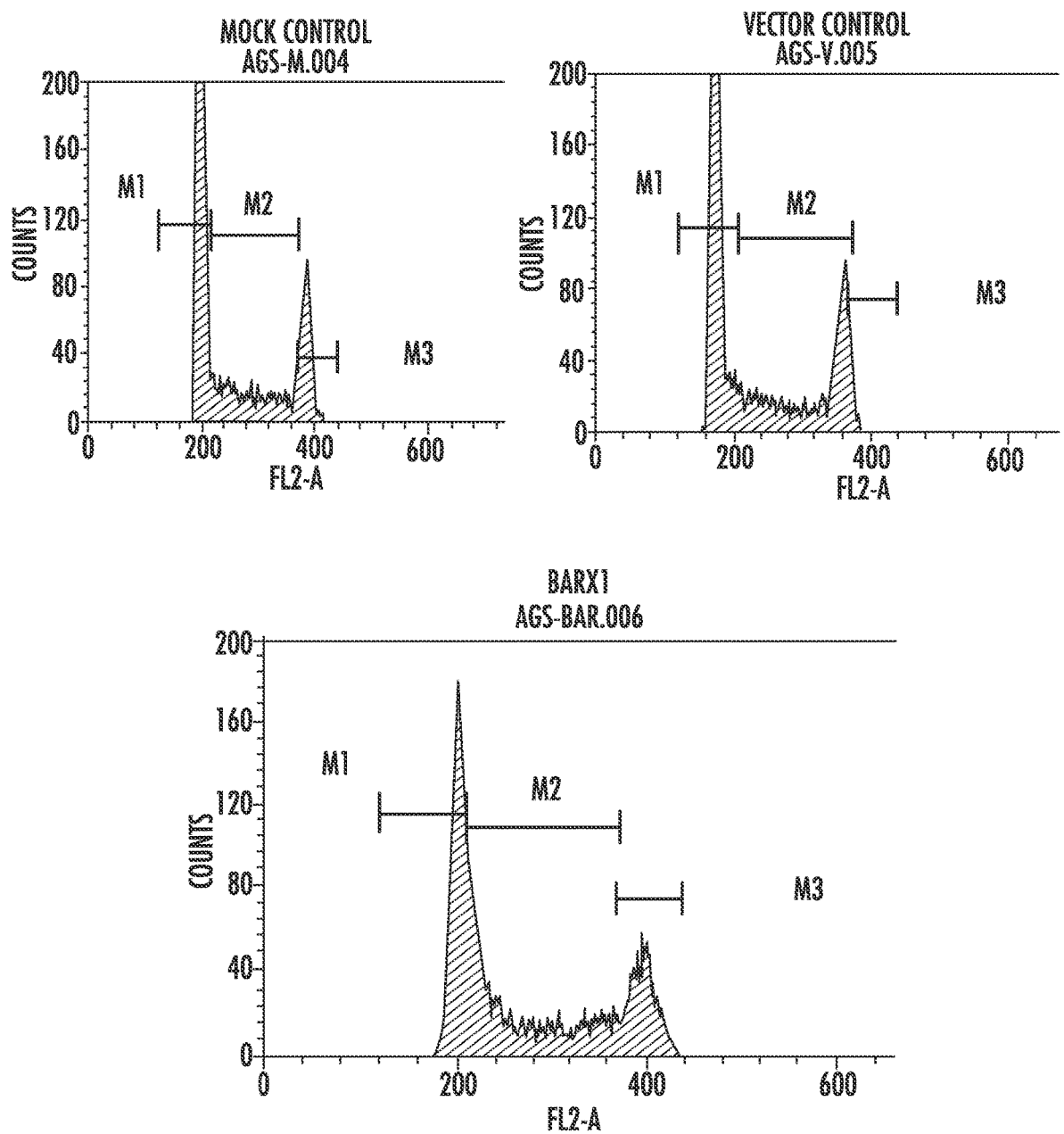
Figure 10:
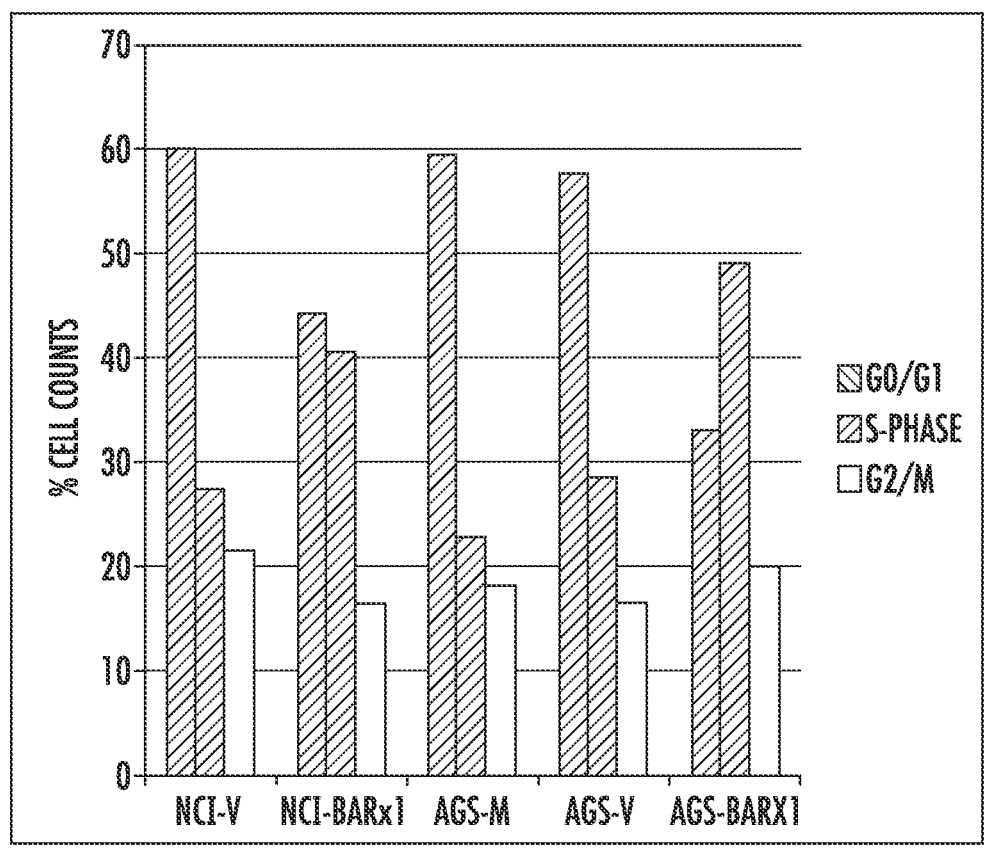
FIG. 10 is a graph showing that Barx1 expression induces S-Phase cell cycle arrest.
Figure 11:
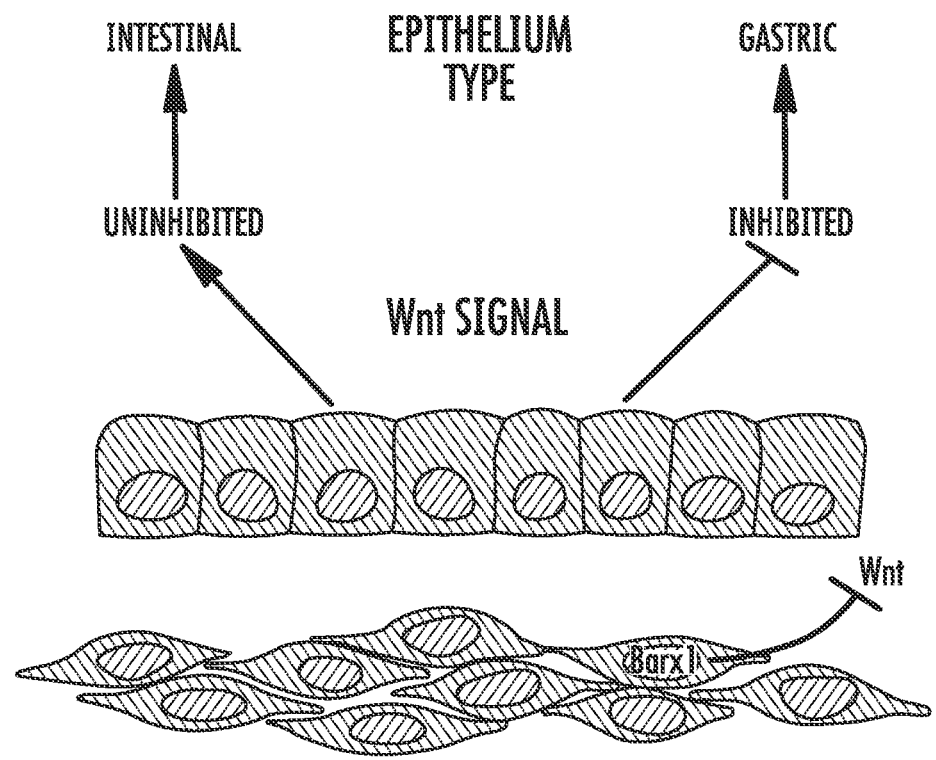
FIG. 11. Barx1 functions as a switch to promote differentiation of a "default" intestinal state into a gastric phenotype. Expression of the homeodomain transcription factor Barx1 is restricted to the developing mesenchyme. Barx1 regulates transcription of many factors, including the secreted inhibitors of Wnt signaling that repress the canonical Wnt pathway in the overlying endoderm. This repression promotes stomach epithelial differentiation at the expense of intestinal differentiation.

Cell Cycle Analysis. GC cells, NCI-N87 and AGS were transgected with BARX1 expressing vector. The cells were harvested after 48 hrs, labelled with propidium iodide and analyzed by DNA flow cytometry. See FIGS. 7, 8 and 9. BARx1 expression may be inducing S-Phase cell cycle arrest (FIG. 10).

Example 2

Characterizing a Homeobox Gene in Gastric Carcinogenesis

Barx1 is a homeobox gene selectively expressed in developing mesenchyme of the gut; it is hypermethylated and silenced in various gastric cancer cell lines. Gastric Cancer is a leading cause of cancer deaths on a global scale, having a five year survival rate below 20%. Using a system of gastric cancer cell lines and normalized cell lines, the present inventors have investigated Barx1 as a candidate Tumor Suppressor Gene (TSG). The data presented in FIGS. 11-16 provide strong evidence regarding the activity of Barx1 as a TSG in GC and lay foundation for further investigations into the downstream effects of this homeobox. The present results indicate that overexpression of Barx1 in gastric cell lines lacking endogenous expression of the gene results in a decrease in cell proliferation and rapid induction of apoptosis.

Cell Culture. Three cell lines were used in this study. HFE145 (immortalized human gastric epithelial cells), MKN28 (differentiated stomach adenocarcinoma cells) and NCI-N87 (metastasis-derived stomach carcinoma).

Tissue Specimens. All patients provided written informed consent under a protocol approved by the Institutional Review Board, Johns Hopkins Hospital (JHH).

siRNA Transfection and RNA Extraction. siRNA designed for Barx1 (Santa Cruz Biotechnologies, USA) was used in siRNA studies. Total RNA from tissue specimens extracted using Trizol reagent (Invitrogen, USA). Total RNA from cells extracted using Rneasy (QIAgen, USA). cDNA synthesis was conducted using Revert Aid™ First Strand cDNA Synthesis Kit (Fermatas). All PCRs were performed in triplicate. GAPDH was used to normalize mRNA expression levels.

Cell Proliferation Assay. Cell proliferation rates were measured using WST-1 assay (Roche, Mannheim, Germany). Optical density was measured using a plate reader (Molecular Devices, Sunnyvale, Calif., USA) after 1 h. incubation (37° C., 5% $CO_2$).

Cell Apoptosis Assay. 24 h and 30 h post-transfection with Barx1 plasmid insert (Origene, Rockville, Md., USA). MKN28 cells were harvested and stained with Annexin V-APC and 7-AAD using Annexin V-APC/7-AAD Apoptosis Detection Kit (BD Biosciences, USA) following the protocol as provided by the manufacturer and examined by Flow Cytometry (BD FACSCalibur).

The data shown in FIGS. 11-15 suggest that Barx1 is a TSG. Further, the present data indicates that overexpression of the gene into GC cell lines results in dramatic changes to the cells.

As described herein, 11 prioritized targets of aberrant epigenetic inactivation in gastric neoplasia (GN) were identified, including the tight junction protein claudin-11 (CLDN11), the transcription factor BarH-like homeobox (BARX1), basonuclin1 (BNC1), Coagulation factor C homolog (COCH), filamin C gamma (FLNC), cytoglobin B (CYGB), glutamine-fructose-6-phospahe-transaminase-2 (GFPT2), heat-shock-70 kDa protein-6 (HSPA6), snail homolog 1 (SNAL1), skin calmodulin-related factor (SCARF), and tumor protein p53 binding protein 2 (TP53BP2). The initial validations on some of the targets such as BARX1 and CLDN11 confirmed these genes to be hypermethylated in their promoter region in gastric cancer cell lines and tissues, and their mRNA expression levels to be reduced in gastric cancer tissues and cell lines. More interestingly, these studies demonstrate that overexpression of some of these genes in GC cells which lack endogenous expression leads to dramatic phenotypic changes in the cells.

This unbiased, comprehensive approach, which to the present inventors' knowledge has not yet been undertaken in GC, is not only likely to ultimately provide better predictive biomarkers than were previously available or possible, but will also provide clues to the biologic basis of gastric carcinogenesis.

Example 3

Characterizing CLDN11 in Gastric Neoplastic Progression

Figure 17A:
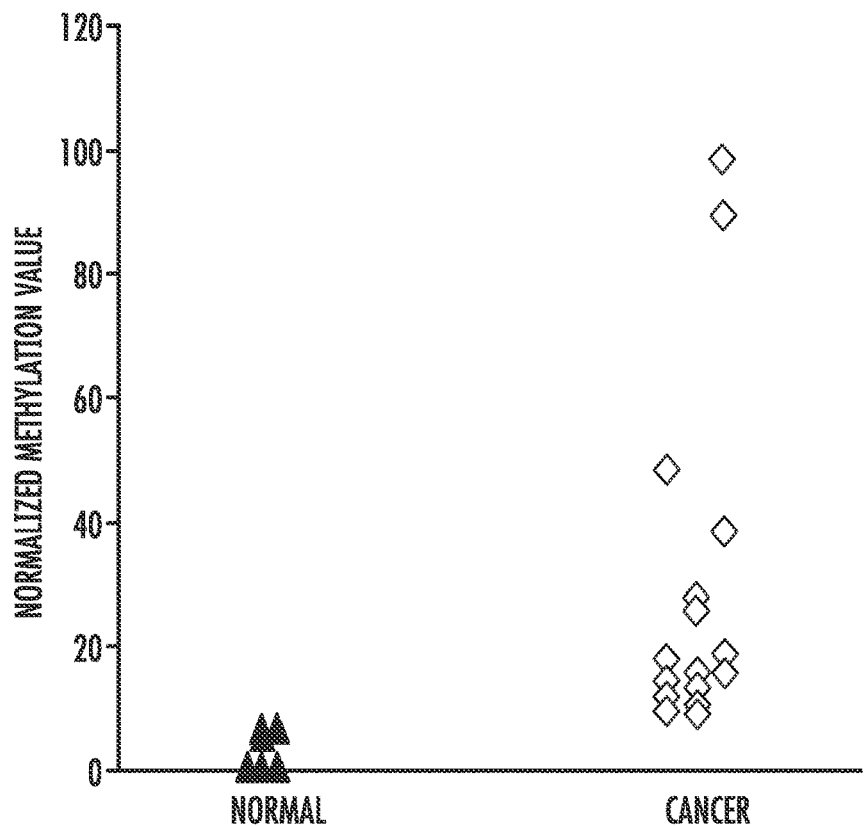
FIG. 17A. qMSP of claudin-11 methylation levels in clinical specimens. P=0.001; n=18 N-T pairs.
Figure 17B:
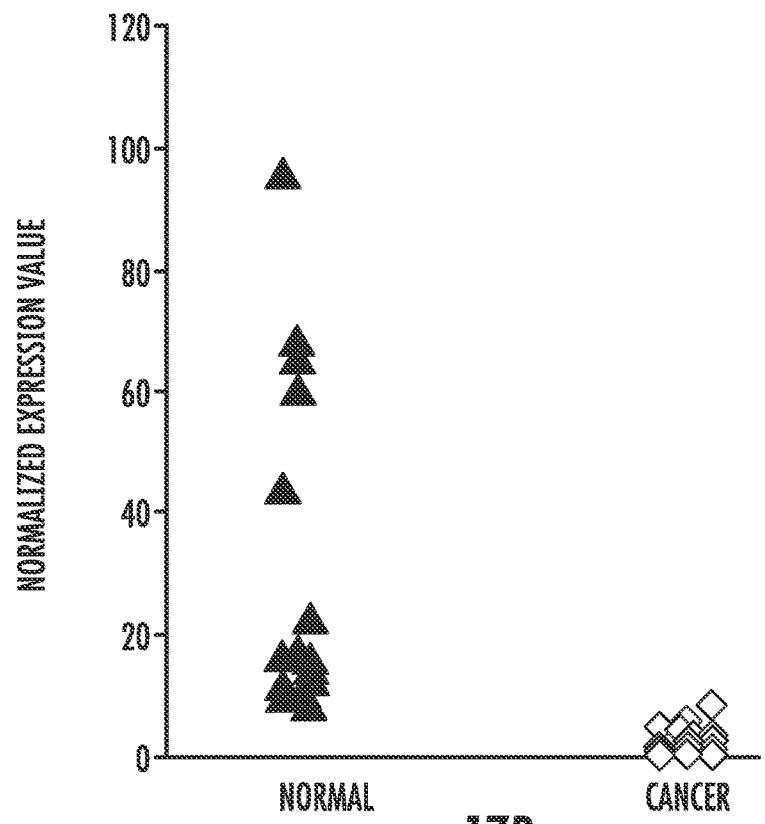
FIG. 17B. CLDN11 mRNA levels in clinical specimens. N=18 N-T pairs. P<0.001, Student's t-test.

First, we tested our hypothesis that the CLDN11 promoter is hypermethylated in primary gastric cancers, and that this methylation correlates inversely with CLDN11 mRNA expression. Genomic DNAs were obtained from 36 clinical specimens, comprising 18 gastric cancers (GC) and 18 paired noncancerous mucosal normal stomach (NS) tissues. CLDN11 promoter methylation levels in these samples were analyzed using quantitative real-time methylation-specific PCR (qMSP). FIG. 17A displays the normalized methylation value (NMV), i.e., the ratio of the CLDN11 methylation value in each specimen to that of a fully methylated control DNA. These results demonstrate that CLDN11 NMVs were significantly higher in GC specimens than in their matching NS tissues (P<0.001). To assess whether CLDN11 promoter hypermethylation in GCs was associated with silencing of CLDN11 expression, CLDN11 mRNA levels were measured using quantitative real-time (qRT-PCR) in RNAs extracted from all 36 specimens used for methylation analysis. As demonstrated in FIG. 17B, after normalization to β-actin, expression values (NEVs) for CLDN11 in GCs were significantly lower than in paired NS samples (P<0.001). This data thus establishes that CLDN11 promoter hypermethylation is associated with silencing of CLDN11 mRNA expression in primary GCs. A scatterplot of NMV vs. NEV revealed a strong inverse correlation between these parameters for CLDN11, confirming the above hypothesis (FIG. 18).

Figure 20:
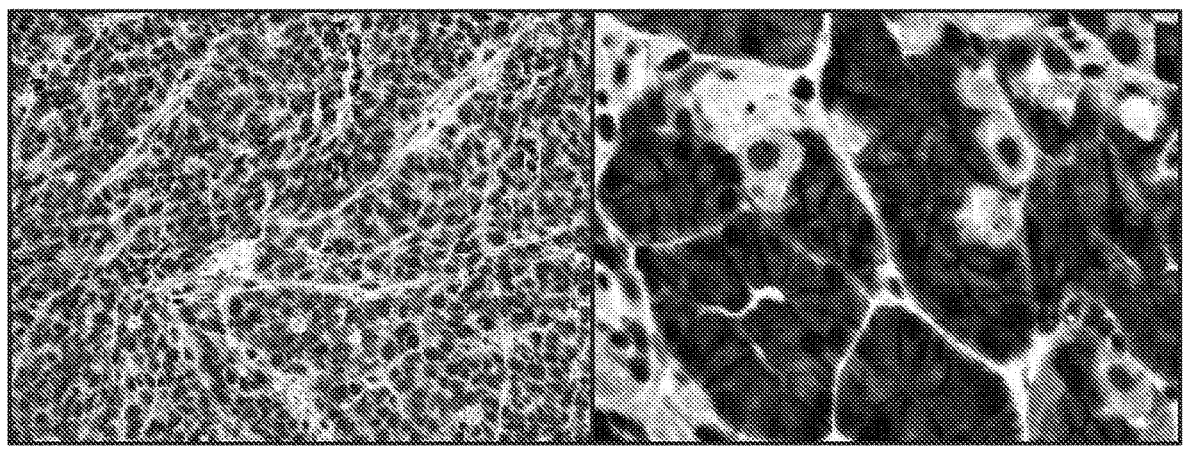
FIG. 20. Immunohistochemical assessment of claudin-11 protein expression in primary gastric cancer (left) and normal stomach (right) tissue specimens.
Figure 24:
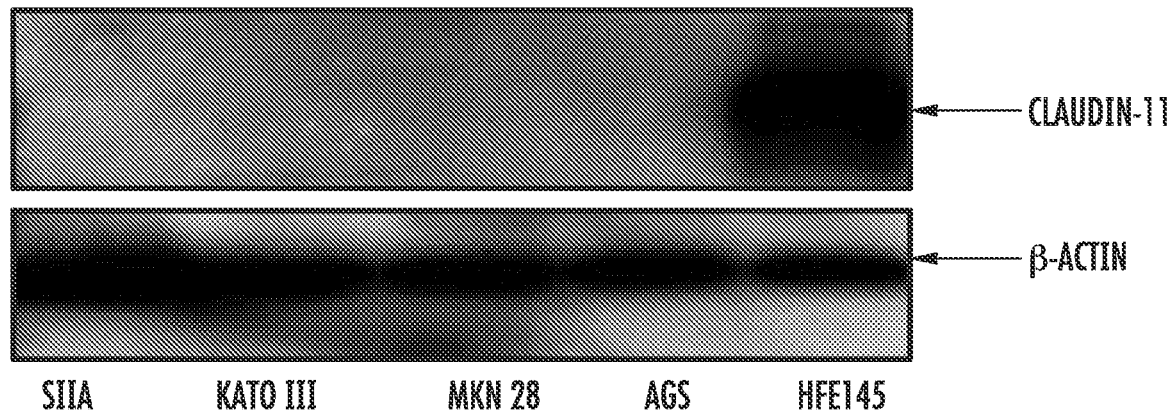
FIG. 24. Western blot of claudin-11 protein expression in gastric cell lines. Western blotting of gastric cell line proteins was performed using an anti-claudin-11 antibody. While HFE145 normal gastric epithelial cells expressed abundant claudin-11 protein, it was not detected in GC cell lines. Anti-β-actin antibody served as a loading control.

We also performed analogous qMSP and qRT-PCR assays of BARX1 in the same 18 NS-GC pairs (FIG. 19). We have also begun to perform Western blotting and immunohistochemical assays to confirm expression of these two methylation target proteins in normal gastric mucosa (NS), as well as to prove silencing of their expression at the protein level in GCs. FIGS. 20 and 24 exemplify our findings.

Example 4

Figure 21:
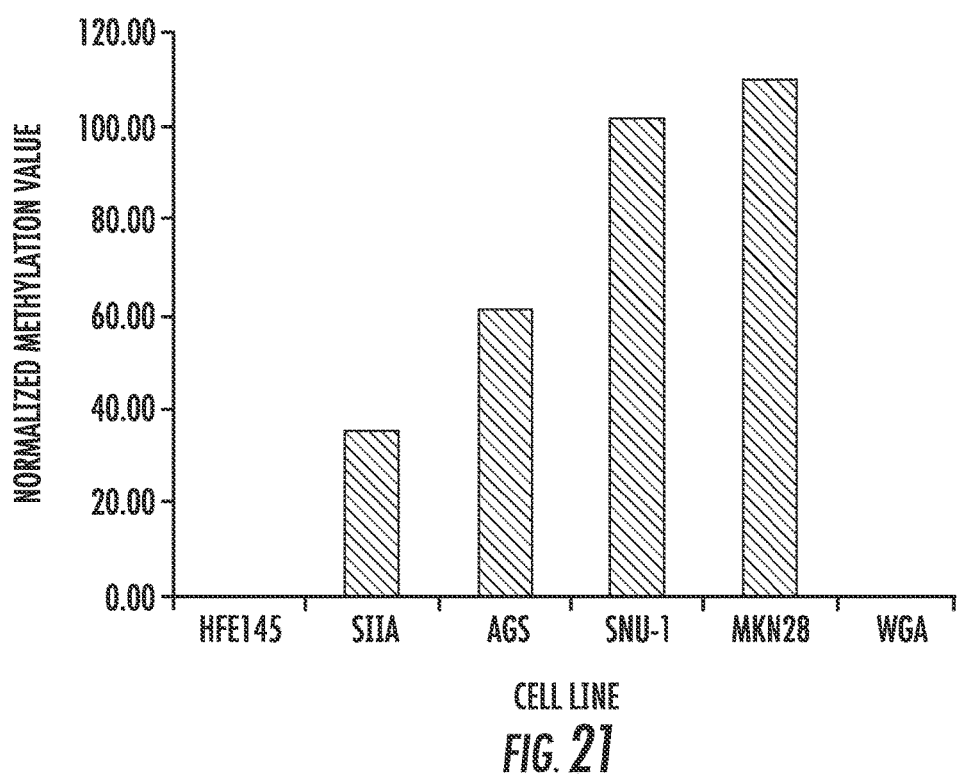
FIG. 21. Quantitative methylation-specific PCR (qMSP) for claudin-11 (above). This figure illustrates the promoter methylation status of claudin-11, a gene identified as hypermethylated in all GC cell lines relative to HFE145 normal gastric epithelial cells (NGECs). Genomic DNAs from these lines were subjected to qMSP. Normalized methylation value (NMV) was defined as follows: NMV=(CLDN11-S/CLDN11-FM)/(ACTB-S/ACTB-FM)*100, where CLDN11-S and CLDN11-FM represent CLDN11 methylation levels in the sample and fully methylated DNAs, respectively, while ACTB-S and ACTB-FM correspond to β-actin in the sample and fully methylated DNAs, respectively. Whole-genome amplified DNA (WGA) was used as an unmethylated negative control. As with methylation arrays, qMSP showed all GC cell lines possessing high CLDN11 promoter methylation levels, but no detectable promoter methylation of CLDN-11 in NGECs.

Investigation of the Biological and Therapeutic Functions of CLDN11 in Gastric Carcinogenesis First, we evaluated CLDN11 promoter methylation and expression in gastric cell lines Immortalized human normal gastric epithelial cells (HFE145) and gastric cancer cell lines SIIA, AGS, SNU-1, and MKN28, in addition to WGA fibroblasts, were studied. All GC cell lines tested (SIIA, AGS, SNU-1, and MKN28) exhibited promoter hypermethylation, whereas no methylation was observed in HFE145 or WGA cells (FIG. 21).

Figure 22:
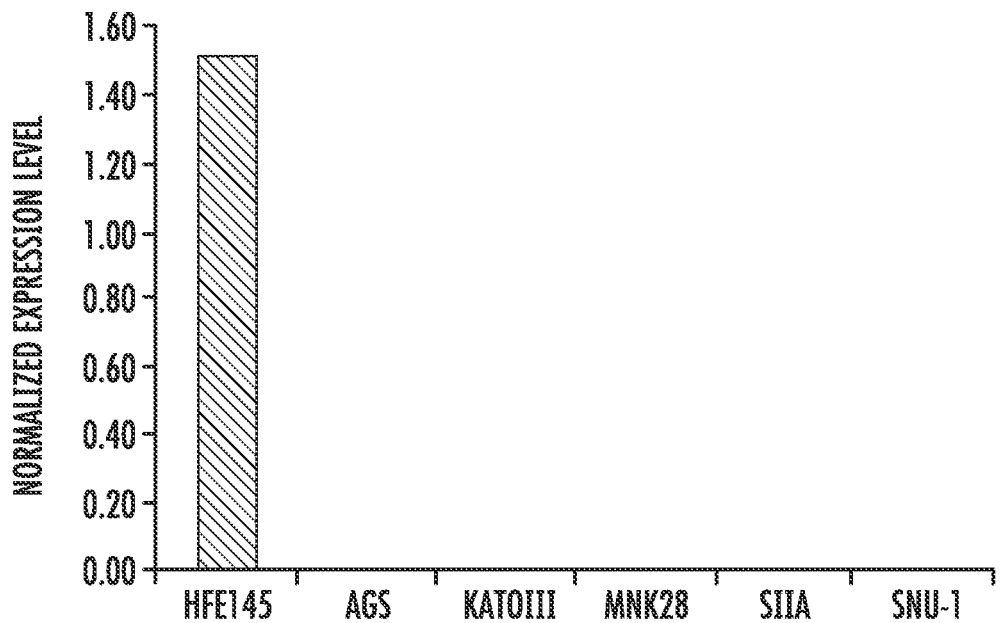
FIG. 22. Claudin-11 mRNA expression in gastric cell lines. Total RNAs from different gastric cell lines were subjected to quantitative real-time RT-PCR analysis Claudin-11 expression was normalized to β-actin expression. HFE145 NGECs expressed very high levels of claudin-11, while all GC cell lines tested exhibited undetectable claudin-11 mRNA.

CLDN11 mRNA levels were assessed by performing qRT-PCRs on RNAs purified from cell lines. As shown in FIG. 22, all 5 GC cell lines exhibited no detectable expression of CLDN11 mRNA, while only HFE145 manifested high CLDN11 expression levels. This finding thus establishes that CLDN11 is coordinately hypermethylated and downregulated in GC cell lines relative to NGECs.

Figure 23:
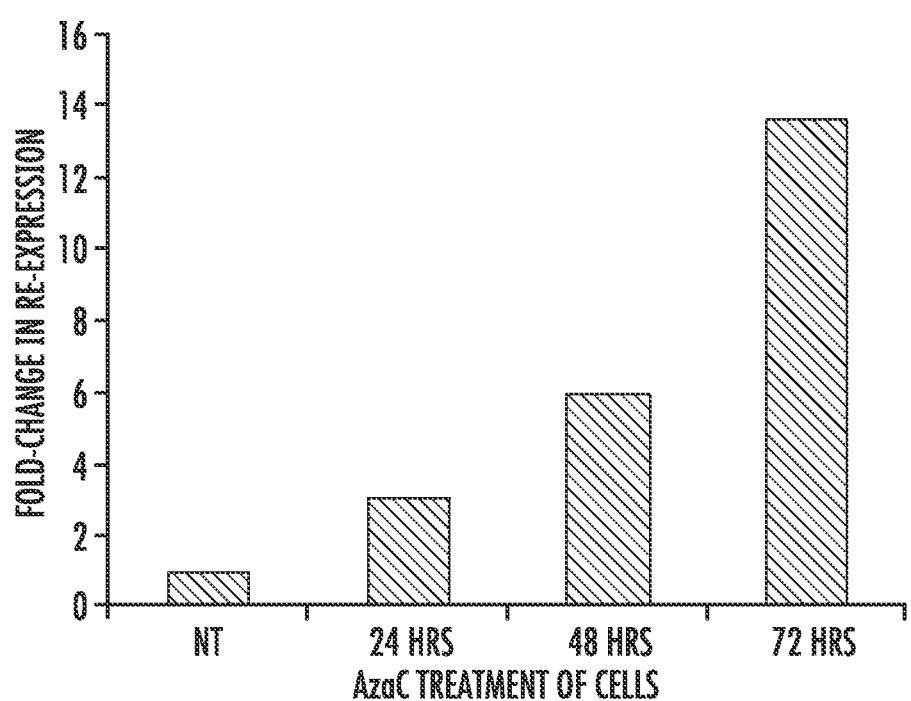
FIG. 23. Claudin-11 mRNA re-expression in AGS gastric cancer cells after treatment with 5-Aza-dC. AGS is a gastric cancer cell line manifesting hypermethylation of the claudin-11 promoter in conjunction with absent claudin-11 mRNA expression (FIG. 17). Total RNAs from AGS cells before and after 5-aza-2-deoxycytidine treatment were subjected to quantitative real-time RT-PCR analysis. The Y-axis represents the expression ratio of 5-aza-dC-treated vs. untreated cells. AGS cells, when treated with 5 μM 5-Aza-dC, exhibited a time-dependent increase in claudin-11 mRNA expression during the first 72 hrs. of treatment. This restoration of claudin-11 expression after 5-Aza-dC treatment supports our hypothesis that claudin-11 is silenced by promoter hypermethylation in GC cells.

To further validate silencing of CLDN11 expression by hypermethylation, we treated the gastric cancer cell line AGS with the demethylating agent, 5-aza-2-deoxycytidine (5-Aza-dC, 1 µM), for varying time intervals. Total RNAs extracted before vs. after treatment were subjected to qRT-PCR for CLDN11. As shown in FIG. 23, at each time point post-Aza-dC, CLDN11 mRNA became more re-expressed, suggesting that CLDN11 is silenced by promoter hypermethylation in AGS GC cells.

Using Western blotting, we also confirmed tumor-specific silencing of CLDN11 expression at the protein level (FIG. 24).

Figure 25:
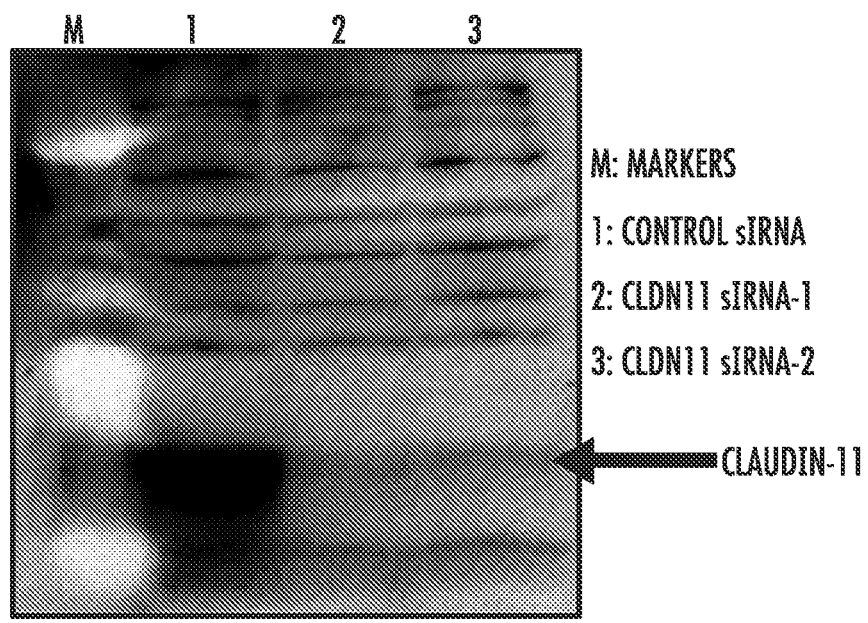
FIG. 25. siRNA-mediated knockdown of claudin-11 protein in HFE145 normal gastric epithelial cells.

Members of the claudin protein family have been implicated in the regulation of cancer cell adhesion, invasion and migration. Therefore, we next investigated whether CLDN11 influences cell motility or invasiveness. HFE145 cells, which express abundant levels of CLDN11, were chosen to study the effects of CLDN11 knockdown on invasive and migratory properties of gastric cells. Transient siRNA transfections were carried out using CLDN11-specific siRNA duplexes. Transfection with specific siRNA duplexes efficiently repressed claudin-11 protein levels by >90%, whereas expression remained unchanged in mock- or nonspecific control siRNA-treated cells (FIG. 25).

Figure 26:
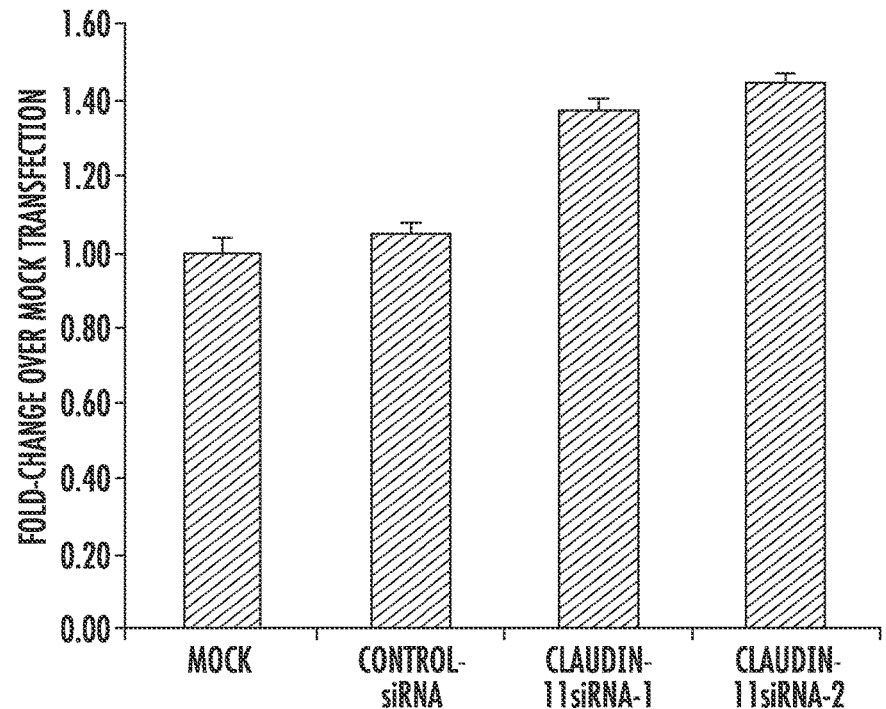
FIG. 26. siRNA-mediated silencing of claudin-11 expression increases proliferation of HFE145 normal gastric epithelial cells.

Cell proliferation assays demonstrated that proliferation was increased in siRNA-treated HFE145 cells, suggesting an antiproliferative function of claudin-11, and supporting our hypothesis that this gene functions as a tumor suppressor in normal stomach epithelium (FIG. 26).

Figure 27:
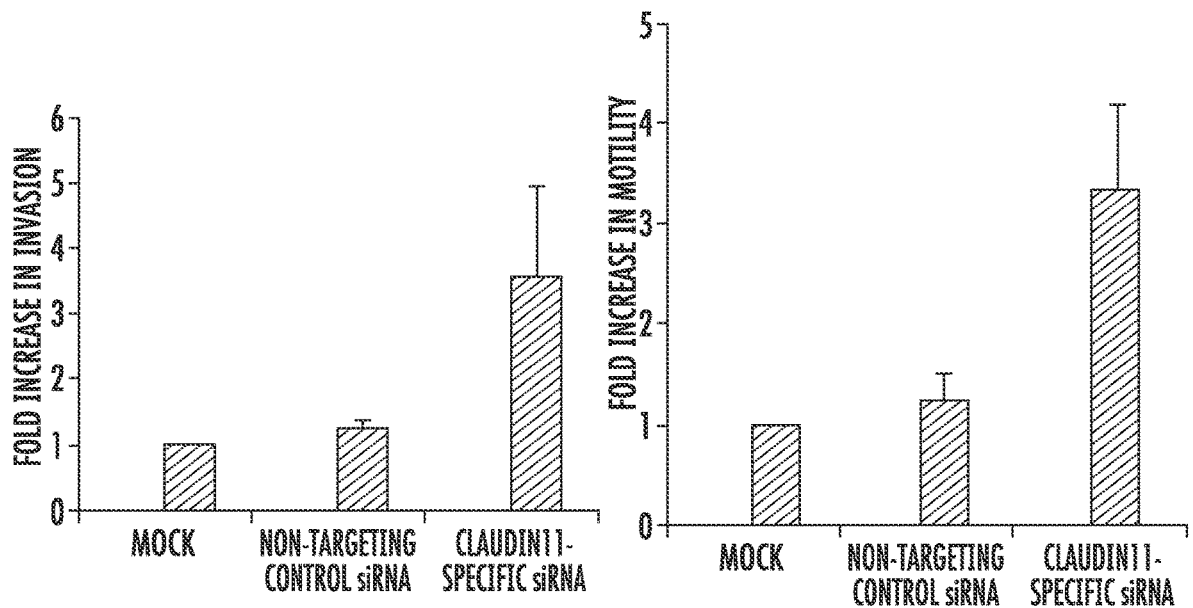
FIG. 27. siRNA-mediated silencing of claudin-11 expression increases invasion and motility of HFE145 normal gastric epithelial cells.

Cell motility and invasion assays were also conducted on siRNA-transfected cells using a modified Boyden chamber assay system. Interestingly, as shown in FIG. 27, inhibition of CLDN11 expression in HFE145 cells significantly increased their invasion and motility.

Figure 28:
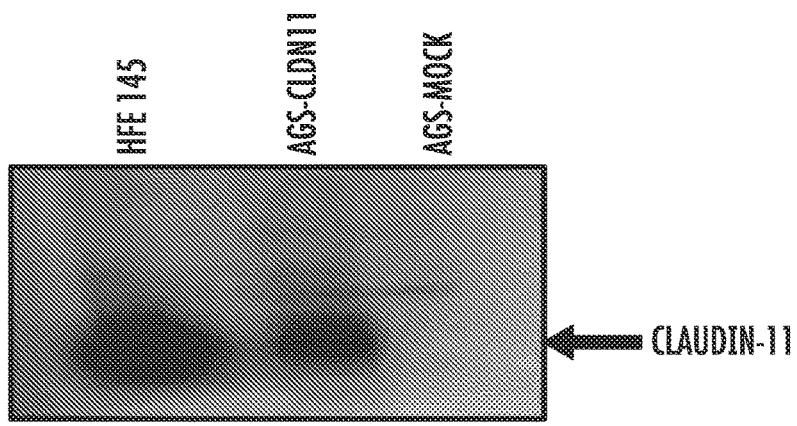
FIG. 28. Western blot analysis of claudin-11 protein expression in transiently transfected AGS cells. AGS cells (which lack endogenous claudin-11) transiently transfected with a full-length wild-type CLDN11 cDNA-containing construct expressed high levels of claudin-11, while mock-transfected control cells expressed no detectable CLDN11 protein. Protein lysates from HFE145 cells were used as a positive control.

We also initiated experiments stably overexpressing LDN11 in GC cells that lacked endogenous CLDN11 expression. Preliminary results of these transfections are illustrated in FIG. 28.

Example 5

To Evaluate the Clinical Relevance of CLDN11 and BARX1 as Early Detection and Prognostic Biomarkers in Gastric Neoplastic Progression More specifically, methylation levels of CLDN11 and BARX1 are measured in tissue samples of normal gastric mucosa (NS), IM, D, and GC, using quantitative real-time methylation-specific PCR (qMSP) and bisulfite pyrosequencing.

Strategy. To assess the clinical significance of CLDN11 and BARX1, these genes are analyzed in patient samples for promoter methylation levels using qMSP. We hypothesize that epigenetic inactivation of these two genes will be clinically relevant as a potential biomarker for early GC detection and prognostication.

Clinical specimens. Paired primary NS, IM, D, and GC tissue samples have been or are collected at the Johns Hopkins Hospital (JHH). Only cases obtained with informed consent as approved by our Institutional Review Board (IRB) are enrolled in this study. Complete clinical data are available from all cases. Examples of types of clinical data available are exemplified in Table 1.

TABLE 1

Examples of clinical data available from patients with gastric cancer.

| ID | Date | Met | Death | Sex | Race | Stage | Age | Location |
|---|---|---|---|---|---|---|---|---|
| 2271 | May 2, 2002 | No | Jul. 26, 2004 | M | Asian | T3N1MX | 83 | body-cardia |
| 2272 | Jul. 11, 2002 | No | | F | B | T1N1MX | 66 | antrum |
| 2273 | Jul. 26, 2001 | No | | M | O | T2N1MX | 48 | |
| 2274 | Dec. 4, 2001 | No | Aug. 15, 2003 | M | W | T2N1MX | 72 | body-cardia |
| 2275 | Jul. 03, 2001 | Yes | Dec. 24, 2003 | F | B | T3N1MX | 80 | body |
| 2276 | Mar. 15, 2001 | Yes | Aug. 15, 2002 | M | W | T2N3MX | 68 | antrum |
| 2277 | Jun. 03, 2003 | No | Feb. 27, 2004 | F | W | T4N2MX | 49 | |
| 2278 | Oct. 19, 2001 | Yes | Apr. 27, 2003 | M | W | T3N1Mx | 67 | body-cardia |
| 2279 | Apr. 24, 2001 | No | | F | W | T3N0Mx | 75 | |
| 2280 | Nov. 15, 2001 | Yes | Jan. 18, 2003 | M | W | T3N1Mx | 60 | |
| 2281 | Oct. 17, 2001 | Yes | Jan. 20, 2007 | M | B | T2N2M1 | 63 | |
| 2282 | Aug. 06, 2002 | No | Aug. 04, 2003 | M | W | T3N3MX | 70 | body |
| 2283 | Dec. 01, 2003 | Yes | | M | B | T4N1MX | 49 | |

TABLE 1-continued

Examples of clinical data available from patients with gastric cancer.

| 2284 | Sep. 17, 2002 | Yes | Apr. 02, 2005 | M | B | T2BN1MX | 49 | |
| 2285 | May 16, 2001 | No | Jun. 16, 2001 | M | W | T2N3MX | 71 | |
| 2286 | Mar. 19, 2003 | No | | F | W | T2BN0MX | 72 | |
| 2287 | Dec. 16, 2002 | Yes | | F | O | T4N1M1 | 23 | |
| 2288 | Nov. 30, 2001 | No | | M | W | T2BN1MX | 62 | |
| 2289 | Feb. 20, 2002 | Yes | Feb. 22, 2003 | M | W | T3N1MX | 83 | |
| 2290 | May 16, 2003 | No | Aug. 18, 2003 | F | W | NA | 66 | body-cardia |

| ID | Pathology - T | Pathology - Non-T | size | AL invasion | PN invasion |
|---|---|---|---|---|---|
| 2271 | MPD | Active CG | 6 | Yes | Yes |
| 2272 | MD, intestinal type | NA | 3 | NA | NA |
| 2273 | MPD w focal SR | marked CG and IM | 3 | NA | NA |
| 2274 | mucinous | NA | 5 | NA | NA |
| 2275 | PD w SR | severe CG w focal IM | 14 | Yes | Yes |
| 2276 | MPD focal SR/colloid | NA | 6 | NA | NA |
| 2277 | PD | NA | 9 | Yes | NA |
| 2278 | PD | NA | NA | Yes | NA |
| 2279 | MD | Atrophic CG w IM | 9 | NA | NA |
| 2280 | PD w SR | NA | 10 | Yes | NA |
| 2281 | PD mucinous w SR | NA | 6.5 | NA | NA |
| 2282 | PD w SR | GEJ w infl/HP polyp | 10 | Yes | Yes |
| 2283 | PD | NA | 9 | NA | NA |
| 2284 | PD w SR | NA | NA | Yes | Yes |
| 2285 | MPD w focal SR | CG w IM | 5.5 | Yes | NA |
| 2286 | PD | NA | 4.5 | No | NA |
| 2287 | SR cellCa | Active CG w *H. pyiori* | 12 | NA | NA |
| 2288 | PD w SR | NA | 2.5 | NA | NA |
| 2289 | PD w SR | NA | 10 | Yes | NA |
| 2290 | PD w anapiasia | NA | 9 | Yes | Yes |

ID, protected research ID; Date, date specimen obtained;
Met, metastases (yes or no);
Death, date of death from any cause;
Race - Asian, black (B), white (W), or other (O);
Pathology - T, histologic grade of gastric tumor;
Pathology - Non-T, histology of nontumor tissue accompanying case;
size, diameter of gastric tumor in cm;
AL invasion, angiolymphatic invasion;
PN invasion, perineural invasion.

Power calculations. To estimate sample size requirements in comparisons of tissues at various stages of neoplastic evolution, we performed 2-sample t-test power calculations at power=0.8 and alpha=0.05 (http://www.stat.uiowa.edu/~rlenth/Power/index.html). As our input data, we used actual mean NMVs and their standard deviations (SDs) generated from our comparison of normal stomach (NS, 1.56±2.54) vs. gastric cancer (GC, 28.59±26.46); with power=0.9 and alpha=0.05, this comparison yielded a sample requirement of 12 per group, easily met with our already collected cases. Next, we made the conservative assumption that mean methylation levels in intestinal metaplasia (IM: 2.74±3.01) would lie closer to those found in NS (again, 1.56±2.54) than to those seen in GC. This power calculation resulted in a sample requirement of 78 per group, numbers already attained for NS and easily attainable for IM within the first 2 years of the study. Similarly, our power calculations for IM vs. dysplasia (D, 16.4±8.7; sample requirement, 7 per group); IM vs. GC (sample requirement, 6 per group); and NS vs. D (sample requirement 6 per group) were well below the numbers of cases already collected. Power calculations for D vs. GC yielded a sample requirement of 23 per group: considering the number of D's already collected and expected per year, this number should also be attainable within the first 2 years of the study.

Patient selection and enrollment. Thus far, we have obtained via endoscopic biopsy or surgery 1293 fresh-frozen tissue or DNA specimens, including 1130 normal gastric epithelia (NS), 112 gastritis (G) specimens, 19 intestinal metaplasia (IM) samples, 10 dysplasia (D) samples, and 286 gastric cancer (GC) specimens. Many of these samples have matched NS, G, IM, D, and/or GC.

In addition to specimens that we have already collected, patients undergoing endoscopy or surgery during the 5-year term of this project are prospectively enrolled after informed consent is obtained. We anticipate that approximately 100 patients per year will present with gastritis, 30 with IM, 10 with D, and 24 with GC (Mark Duncan, Dept. of Surgery; Elizabeth Montgomery, Dept. of Pathology; and Mimi Canto, GI Division, personal communications). All patients have signed or will sign informed consent under an IRB-approved protocol for the use of their tissue specimens in research. In addition, all samples studied will be of uniform quality, tracked, stored, and managed carefully and consistently.

Laser capture microdissection. GNs, particularly metaplastic and dysplastic lesions, can be focal, heterogeneous or contaminated with inflammatory, stromal, endothelial, and benign epithelial elements. Therefore, for all lesions studied, we perform careful microdissection utilizing LCM methodology. Lesions are purified to ensure that the area of interest is properly isolated from its surrounding normal epithelial and nonepithelial components. An additional advantage of this approach is that normal epithelium adjacent to GNs can also be sampled to ascertain whether aberrant methylation occurring in cancer or dysplasia can be detected in histologically normal, but geographically at-risk, epithelia. Therefore, tissues are microdissected using a laser capture microdissection (LCM) device (PixCell II, Arcturus). Frozen sections are prepared by embedding specimens in OCT compound within a disposable plastic mold and cutting with a cryotome. Prior to LCM, thin frozen sections are fixed in 75% ethanol for 30 seconds, then immediately stained with HistoGene Stain (Cat. # KIT 0401, Arcturus, Mountain View, Calif.). After staining, the sections are air-dried for at least 5 minutes. Then, cells from each section are selected by applying multiple laser pulses to each section. For each section, five LCM caps are generated in turn and immediately immersed in RNA protecting buffer (Micro RNA Isolation Kit, cat. #200344, Stratagene, La Jolla, Calif.).

Figure 29:
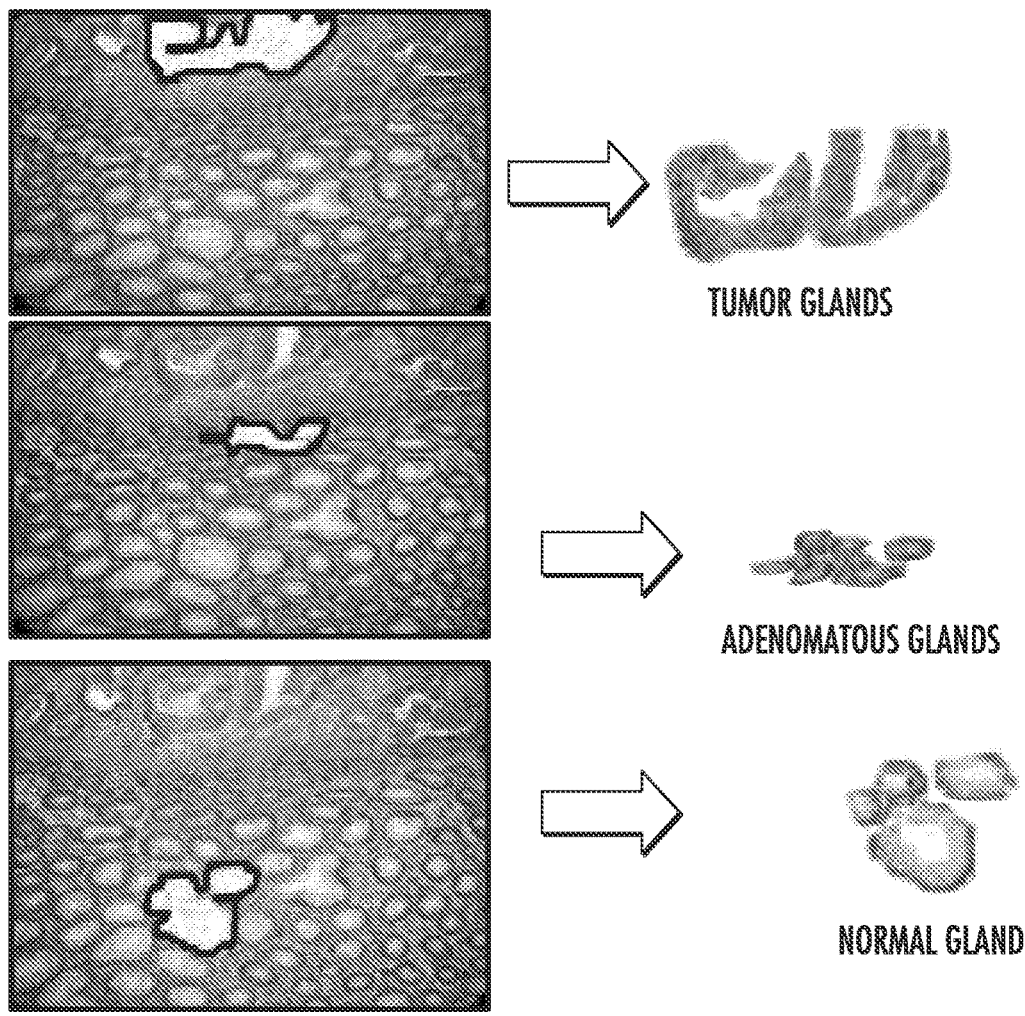
FIG. 29. Laser capture microdissection (LCM). Within all specimens, any available gastric tumor, intestinal metaplasia, dysplasia, and normal gastric mucosa will be separately microdissected, adhered to reaction tube caps using LCM, and analyzed directly. Aliquots of each fresh specimen will be frozen in OCT compound and placed in cassettes. Sections will be cut on a cryotome, transferred to slides, and immediately fixed in a mixture of 3 parts 70% ethanol to 1 part 100% methanol for 2 minutes. Fixed sections will be stained with hematoxylin and eosin, dried, and subjected to microdissection on an Arcturus PixCell II LCM apparatus.

We separately microdissect each lesion or histologic cell type, adhere the microdissected area to Eppendorf reaction tube caps using the laser within the LCM device, and then perform DNA extraction in Eppendorf reaction tubes. Our preliminary data using LCM-dissected tissues shows that can successfully perform microarray studies on LCM-derived material. This strategy is illustrated in FIG. 29.

Assessment of Promoter Methylation Status Using Quantitative Real-Time Methylation-Specific PCR (qMSP) and Bisulfite Pyrosequencing.

Genomic DNA preparation. Genomic DNA is extracted from snap-frozen tissue samples using the DNeasy Blood & Tissue Kit (QIAGEN, Valencia, Calif.) according to the manufacturer's protocol. Extracted DNAs is quantified using a NanoDrop ND-1000 Spectrophotometer.

Quantitative methylation-specific PCR (qMSP). An MSP amplicon and TaqMan probe to detect completely methylated DNA is utilized for each gene to include multiple CpG sites in its 5'-UTR region. qMSP is performed as described previously, with minor modifications (Mori et al., 131 GASTROENTEROLOGY 797-808 (2006)). Duplex PCR with β-actin primer and probe sequences containing no CpGs are performed for normalization.

Bisulfite pyrosequencing. As a second approach, we perform bisulfate pyrosequencing. One of the biggest advantages conferred on DNA methylation analysis by pyrosequencing is its robust, high-throughput, accurate quantification of methylation levels at all individual CpG sites within a given DNA segment.

Expression Levels of CLDN11 and BARX1 Will be Compared in Tissue Samples of Normal Gastric Mucosa (NS), IM, D, and GC, Using Quantitative Real-Time Reverse Transcriptase PCR (qRT-PCR) and Immunohistochemistry.

Strategy. To test our hypothesis that CLDN11 and BARX1 promoter hypermethylation in is inversely correlated with their mRNA expression in primary gastric cancer tissues, we compare the mRNA expression levels in the various gastric tissue specimens using quantitative real-time reverse transcriptase PCR (qRT-PCR). Next, we determine whether hypermethylation and transcriptional inactivation of a candidate gene translates to reduced or absent protein expression. Moreover, since the biopsy specimens used for DNA and RNA studies (methylation and expression analysis) may contain nonepithelial cells, in order to localize the candidate gene under study, we conduct immunohistochemical staining of tissue microarrays, using specific antibodies.

Quantitative real-time RT-PCR. Purification and preparation of RNA: Total RNA from gastric tissue specimens and cell lines is extracted using an RNAeasy kit (Qiagen, Valencia, Calif. 913555, cat. no. 74104). The quality of total RNA is assessed using an Agilent 2100 Bioanalyzer (Agilent, Palo Alto, Calif.). An ND-1000 Spectrophotometer (NanoDrop, Wilmington, Del.) will be used to quantitate RNA in each sample. qRT-PCR: Each RT-PCR amplicon is designed to overlap an intron-exon boundary in order to exclude gDNA amplification. One-step qRT-PCR is performed as described by us previously (Colella et al., 35 BIOTECHNIQUES 146-50 (2003); Tost et al., 35 BIOTECHNIQUES 152-56 (2003)), using a Quantitect SYBRA RT-PCR kit (QIAGEN, Valencia, Calif.) according to the manufacturer's protocol. Tissue arrays and immunohistochemical (IHC) studies: Protein expression levels of candidate genes is assessed by IHC, using gastric tissue arrays provided by our collaborator (Dr. Elizabeth Montgomery, Department of Pathology, JHU). A description of these gastric tissue arrays has been published (Cunningham et a., 15 CANCER EPIDEMIOL. BIOMARKERS PREV. 281-87 (2006)) Immunohistochemical staining is performed using a streptavidin-peroxidase procedure, following the manufacturer's protocol (Dako Corp., Carpinteria, Calif.). Staining will be evaluated as described by us previously.

The Ability of CLDN11 and BARX1 Methylation Levels to Function as Biomarkers Distinguishing Between NS, IM, D, and GC Will be Tested by Pairwise Comparisons and ROC Curves.

Strategy and Methods: Our laboratory is intimately familiar with developing and validating biomarkers to distinguish among clinical disease stages or disease risk categories (Sato et al., 3 PLoS ONE e1890 (2008); Schulmann et al., 24 ONCOGENE 4138-48 (2005)). Of specific relevance to the current application, we have tested multiple methylation events for their timing and biomarker value in esophageal adenocarcinogenesis (EACG) (Jin et al., 123 INTL., J. CANCER 2331-36 (2008); Jin et al., 17 CANCER EPIDEMIOL. BIOMARKERS PREV. 111-17 (2008); Jin et al., 112 CANCER 43-9 (2008); Sato et al., 3 PLoS ONE e1890 (2008); Jin et al., 26 ONCOGENE 6332-40 (2007); Jin et al., 13 CLIN. CANCER RES. 6293-6300 (2007); Schulmann et al., 24 ONCOGENE 4138-48 (2005)). These studies established that several genes were methylated early in EACG, that panels of genes can accurately predict future neoplastic progression in BE (Jin et al., "A multicenter, double-blinded pre-validation study of methylation biomarkers for progression prediction in Barrett's esophagus," CANCER in press; Sato et al., 3 PLoS ONE e1890 (2008)), and that methylation biomarkers can predict the prognosis and response to chemoradiotherapy of patients with EAC (Hamilton et al., 4 CLIN. GASTROENTEROL. HEPATOL. 701-08 (2006). In these studies, we used paired t-testing and receiver-operator characteristic (ROC) curves to estimate the performance of these biomarkers.

We apply analogous methods in the current application to determine the ability of CLDN11 and BARX1 methylation levels to distinguish NS from IM, IM from D, D from GC, NS from D, NS from GC, and IM from GC. These comparisons establish the potential value of these methylation events as early detection biomarkers. In addition, we correlate initial CLDN11 and BARX1 methylation levels at the time of diagnosis with clinical follow-up parameters, including overall survival, disease-free survival, response to therapy, interval to disease recurrence, and interval to disease progression in patients with frank GC, as described by us previously (Hamilton et al., 4 CLIN. GASTROENTEROL. HEPATOL. 701-08 (2006); Kawakami et al., 92 J. NATL. CANCER INST. 180511 (2000)).

We claim:

1. A method comprising the steps of (a) measuring the methylation levels of the promoter region of a panel of genes in a sample collected from a patient, wherein the panel comprises BarH-like homeobox (BARX1), cytoglobin B (CYGB), claudin-11 (CLDN11) and snail homolog 1 (SNAL1); and (b) administering a demethylating agent to a patient having hypermethylation in the promoter region of one or more of the genes in the panel, wherein the patient is suspected of having gastric cancer.

2. The method of claim 1, wherein the panel further comprises one or more of basonuclin1 (BNC1), coagulation factor C homolog (COCH), filamin C gamma (FLNC), glutamine-fructose-6-phospahe-transaminase-2 (GFPT2), heat-shock-70 kDa protein-6 (HSPA6), skin calmodulin-related factor (SCARF), and tumor protein p53 binding protein 2 (TP53BP2).

3. The method of claim 1, wherein the sample is a blood or serum sample.

4. The method of claim 1, further comprising the step of administering a chemotherapeutic treatment regimen to a patient having hypermethylation in the promoter region of one of more of the genes in the panel, wherein the patient is suspected of having gastric cancer.

5. A method comprising the steps of:
   a. performing bisulfite modification to nucleic acid obtained from a sample taken from a patient, wherein the sample is from a specimen selected from the group consisting of tissue specimen, biopsy specimen, a surgical specimen, blood, plasma, serum, saliva and a cytological specimen; and
   b. performing quantitative methylation specific PCR (qMSP) on the bilsulfite modified nucleic acid from step (a) using primers specific for the promoter region of a panel of genes comprising BARX1, CYGB, CLDN11, and SNAL1.

6. The method of claim 5, wherein the panel further comprises one more of BNC1, COCH, FLNC, GFPT2, HSPA6, SCARF, and TP53BP2.

7. The method of claim 5, wherein the sample is a blood or serum sample.

8. The method of claim 5, further comprising the step of administering a demethylating agent to a patient having hypermethylation in the promoter region of one or more of the genes in the panel, wherein the patient is suspected of having gastric cancer.

9. The method of claim 8, further comprising the step of administering a chemotherapeutic treatment regimen to a patient having hypermethylation in the promoter region of one of more of the genes in the panel, wherein the patient is suspected of having gastric cancer.

10. A method comprising the steps of:
    a. performing bisulfite modification to nucleic acid obtained from a sample taken from a patient, wherein the sample is from a specimen selected from the group consisting of tissue specimen, biopsy specimen, a surgical specimen, blood, plasma, serum, saliva and a cytological specimen; and
    b. PCR amplifying the bilsulfite modified nucleic acid from step (a) using primers specific for the promoter region of a panel of genes comprising BARX1, CYGB, CLDN11, and SNAL1; and
    c. performing pyrosequencing on the amplified nucleic acids.

11. The method of claim 10, wherein the panel further comprises one more of BNC1, COCH, FLNC, GFPT2, HSPA6, SCARF, and TP53BP2.

12. The method of claim 10, wherein the sample is a blood or serum sample.

13. The method of claim 10, further comprising the step of administering a demethylating agent to a patient having hypermethylation in the promoter region of one or more of the genes in the panel, wherein the patient is suspected of having gastric cancer.

14. The method of claim 13, further comprising the step of administering a chemotherapeutic treatment regimen to a patient having hypermethylation in the promoter region of one of more of the genes in the panel, wherein the patient is suspected of having gastric cancer.

* * * * *